United States Patent
Cai et al.

(10) Patent No.: US 9,234,007 B2
(45) Date of Patent: Jan. 12, 2016

(54) RGD MIMETIC γ-AAPEPTIDES AND METHODS OF USE

(71) Applicants: Jianfeng Cai, Tampa, FL (US); Youhong Niu, Tampa, FL (US); Weibo Cai, Madison, WI (US); Hao Hong, Madison, WI (US)

(72) Inventors: Jianfeng Cai, Tampa, FL (US); Youhong Niu, Tampa, FL (US); Weibo Cai, Madison, WI (US); Hao Hong, Madison, WI (US)

(73) Assignees: UNIVERSITY OF SOUTH FLORIDA, Tampa, FL (US); WISCONSIN ALUMNI RESEARCH FOUNDATION, Madison, WI (US)

( * ) Notice: Subject to any disclaimer, the term of this patent is extended or adjusted under 35 U.S.C. 154(b) by 34 days.

(21) Appl. No.: 13/920,693

(22) Filed: Jun. 18, 2013

(65) Prior Publication Data
US 2014/0004039 A1    Jan. 2, 2014

Related U.S. Application Data

(60) Provisional application No. 61/667,035, filed on Jul. 2, 2012.

(51) Int. Cl.

| | |
|---|---|
| *A61K 51/00* | (2006.01) |
| *A61M 36/14* | (2006.01) |
| *C07K 7/64* | (2006.01) |
| *C07K 5/08* | (2006.01) |
| *A61K 51/08* | (2006.01) |
| *C07K 5/02* | (2006.01) |
| *C07K 5/09* | (2006.01) |

(52) U.S. Cl.
CPC . *C07K 7/64* (2013.01); *A61K 51/08* (2013.01); *A61K 51/088* (2013.01); *C07K 5/0215* (2013.01); *C07K 5/08* (2013.01); *C07K 5/0817* (2013.01); *A61K 51/082* (2013.01)

(58) Field of Classification Search
None
See application file for complete search history.

(56) References Cited

U.S. PATENT DOCUMENTS

| 5,955,572 A | 9/1999 | Ruoslahti et al. |
|---|---|---|
| 6,815,426 B2 | 11/2004 | Scialdone et al. |
| 7,795,386 B2 | 9/2010 | Corti et al. |
| 7,928,113 B2 | 4/2011 | Neamati et al. |
| 8,834,840 B1 * | 9/2014 | Bull et al. ................ 424/1.69 |
| 2009/0148459 A1 | 6/2009 | Woessner et al. |
| 2010/0074844 A1 | 3/2010 | Kolb et al. |

OTHER PUBLICATIONS

Niu et al. (New J. Chem. 2011, 35, 542-545).*
Niu et al. (Org. Biomol. Chem. 2011, 9, 6604-6609).*
Hart et al. (Gene Therapy 1997, 4, 1225-1230).*
Haubner, et al. Radiolabeled Tracers for Imaging of Tumor Angiogenesis of Anti-Angiogenic Therapies, vol. 10, No. 13, May 2004, pp. 1439-1455 (17), Current Pharmaceutical Design.
Carlos Mas-Moruno, et al.; Cilengitide: The First Anti-Angiogenic Small Molecule Drug Candidate. Design, Synthesis and Clinical Evaluation; Anti-Cancer Agents in Medicinal Chemistry, 2010, 10, 753-768.
David A. Reardon, et al.; Cilengitide: an RGD pentapeptide avB3 and avB5 integrin inhibitor in development for glioblastoma and other malignancies; Future Oncol.; 2011; 7(3); 339-354.
Christina Hultsch, et al.: F-Flouroglucosylation of peptides, exemplified on cyclo(RGDfK); Eur J Nucl Med Mol Imaging; 2009; 36: 1469-1474.
Zhaofei Liu, et al.; Noninvasive imaging of tumor integrin expression using F-labeled RGD dimer peptide with PEG4 linkers; Eur J Nucl Med Mol Imaging; 2009; 36: 1296-1307.
Roland Haubner, et al.: Galacto-RGD: Synthesis, Radiolabeling, Metabolic Stability, and Radiation Does Estimates; Bioconjugate Chem 2004, 15, 61-69.
Wang, et al.: Development of NGR-Based Anti-Cancer Agents for Targeted Therapeutics and Imaging; Anti-Cancer Agents in Medicinal Chemistry, 2012, 12, 000-000.

* cited by examiner

*Primary Examiner* — Michael G Hartley
*Assistant Examiner* — Melissa Perreira
(74) *Attorney, Agent, or Firm* — Thomas Horstemeyer LLP

(57) ABSTRACT

Embodiments of the present disclosure provide for RGD mimetic γ-AApeptide compounds, γ-AApeptide compounds capable of binding an RGD binding site on integrin $\alpha_v\beta_3$, linear γ-AApeptide compounds, cyclic γ-AApeptide compounds and multimeric RGD mimetic γ-AApeptide compounds, methods of making each, and methods of using each, and the like. In embodiments, the RGD mimetic γ-AApeptide compounds can be used in imaging, diagnostics, and treatment of angiogenesis related conditions.

11 Claims, 9 Drawing Sheets

RGD MIMETIC γ-AAPEPTIDES AND METHODS OF USE

CROSS-REFERENCE TO RELATED APPLICATION

This application claims priority to U.S. provisional application entitled "RGD Mimetic γ-AAPeptides and Methods of Use," having Ser. No. 61/667,035, filed on Jul. 2, 2012, which is entirely incorporated herein by reference.

BACKGROUND

Cancer causes about fifteen % of all human deaths worldwide. Early detection and treatment will lead to the improved survival for various cancers. However, the development of many cancers is still poorly understood, and drugs have not been proven to be generally efficient in the treatment of cancers. Positron emission tomography (PET) has been widely used in clinical oncology for tumor diagnosis, staging, and treatment monitoring. Development and clinical translation of novel, molecularly targeted PET tracers will facilitate future developments in personalized medicine for cancer patients, such as patient stratification and monitoring the therapeutic responses to anti-cancer drugs. Non-invasive PET imaging of tumor angiogenesis (e.g., new blood vessel formation) has gained tremendous interest over the last decade, since the development and metastasis of solid tumors depends on tumor angiogenesis.

Angiogenesis is a fundamental biological process involved in the growth of most solid tumors; as such, anti-angiogenic approaches, such as the development of angiogenesis inhibitors represents a promising strategy for cancer treatment, diagnosis, and prevention. Integrins, a family of heterodimeric cell surface receptors involved in a wide range of cell-cell and cell-extracellular matrix interactions, including tumor angiogenesis, have been active targets for development of anti-angiogenic therapies.

Among the many proteins involved in tumor angiogenesis and metastasis of solid tumors, integrin $\alpha_v\beta_3$ is one of the most intensively studied. Several PET tracers targeting this cell adhesion molecule have entered clinical investigation. Frequently overexpressed on the tumor neovasculature, as well as cancer cells of many tumor types (e.g., lung/prostate/breast cancer and glioblastoma), integrin $\alpha_v\beta_3$ is an attractive target for both cancer diagnosis and therapy. Integrin $\alpha_v\beta_3$ binds tightly to ECM proteins such as fibronectin, fibrinogen, and vitronectin, which contain the tripeptide sequence RGD (Arg-Gly-Asp), a prominent recognition motif involved in cell adhesion. Since $\alpha_v\beta_3$ is highly upregulated on the endothelium during tumor angiogenesis, peptides or small non-peptidic molecules mimicking the RGD recognition motif may represent promising anti-angiogenesis agents by targeting $\alpha_v\beta_3$ for cancer prevention or targeted diagnosis.

SUMMARY

Embodiments of the present disclosure provide for novel RGD mimetic γ-AApeptides, methods of using the γ-AApeptides, and methods of making the γ-AApeptides.

Embodiments of compounds of the present disclosure include a peptidomimetic compound including a γ-AApeptide capable of binding an RGD binding site.

In embodiments, the present disclosure includes γ-AApeptide compounds capable of binding an RGD binding site on integrin $\alpha_v\beta_3$. In embodiments, the γ-AApeptide compounds of the present disclosure capable of binding an RGD binding site on integrin $\alpha_v\beta_3$ include γ-AApeptides having the structure of Formula I:

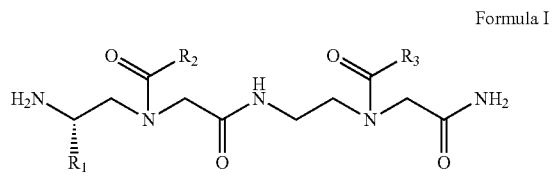

Formula I where R1 is a moiety selected from the following:

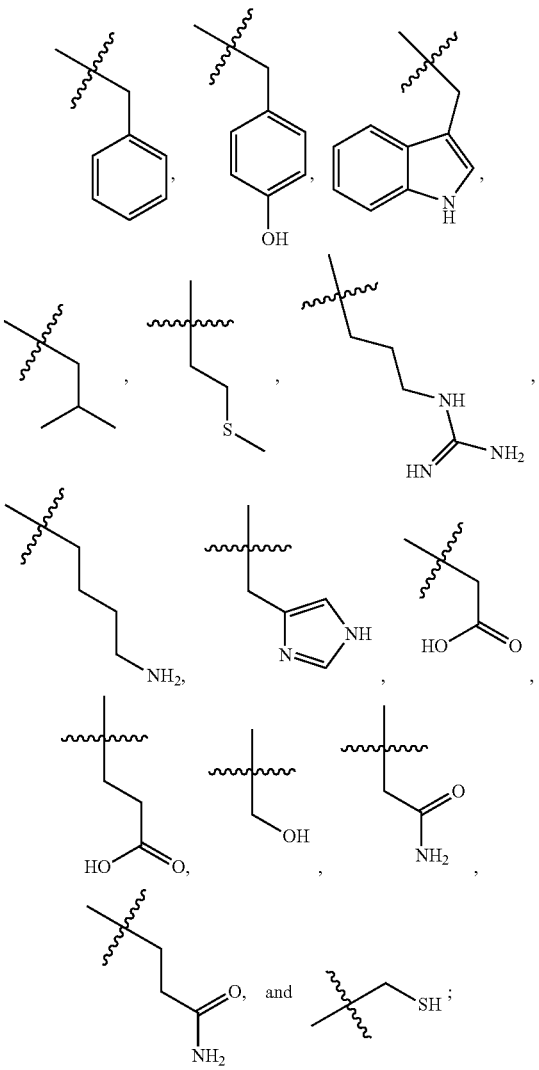

where R2 is a moiety selected from the following:

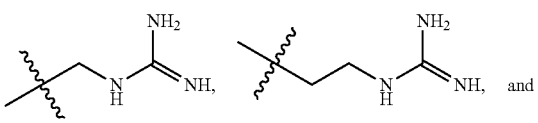

-continued

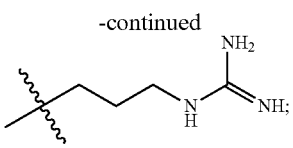

and
where R3 is a moiety selected from the following:

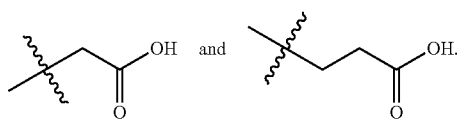 [SMILES: *CC(=O)O ; "and" ; *CCC(=O)O]

In embodiments, the γ-AApeptide compound is a multimeric γ-AApeptide compound having two or more γ-AApeptide units of Formula I joined by a linker. In yet other embodiments of the present disclosure, the γ-AApeptide compound includes a cyclic γ-AApeptide. In embodiments the cyclic γ-AApeptide is a cyclic pentapeptide or a cyclic hexapeptide.

The present disclosure also includes γ-AApeptide compounds having a detectable label coupled to the γ-AApeptide. In embodiments, the detectable label is coupled to the γ-AApeptide via a linker.

Embodiments of the present disclosure also include a kit containing a γ-AApeptide compound coupled to a detectable label and instructions for use of the labeled γ-AApeptide compound, where the γ-AApeptide compound has the structure of Formula I.

The present disclosure also includes pharmaceutical compositions including a γ-AApeptide compound or a pharmaceutically acceptable salt, solvate or hydrate thereof, and a pharmaceutically acceptable carrier, where the γ-AApeptide compound is capable of binding an RGD binding site on integrin $\alpha_v\beta_3$.

Embodiments of methods of detecting integrin $\alpha_v\beta_3$ in a host or a tissue according to the present disclosure include administering to the tissue or host a detectably effective amount of a radiolabeled γ-AApeptide compound including a radiolabel coupled to a γ-AApeptide compound of the present disclosure capable of binding an RGD binding site on integrin $\alpha_v\beta_3$. The method further includes using an imaging system employing PET for detecting distribution of the radiolabeled γ-AApeptide compound within the host or tissue, where the detection of the radiolabeled γ-AApeptide compound indicates the presence of integrin $\alpha_v\beta_3$ in the host or tissue.

Methods of the present disclosure also include methods of imaging angiogenesis in a host or a tissue. In embodiments, such methods include administering to the tissue or host a detectably effective amount of a radiolabeled γ-AApeptide compound, the radiolabeled γ-AApeptide compound including a radiolabel coupled to a γ-AApeptide compound capable of binding an RGD binding site on integrin $\alpha_v\beta_3$. The method also includes using an imaging system employing PET for detecting distribution of the radiolabeled γ-AApeptide compound within the host or tissue, where the detection of the radiolabeled γ-AApeptide compound indicates the location of angiogenesis in the host or tissue. In embodiments, detection of angiogenesis in the host or tissue indicates the presence of one or more angiogenesis-related diseases or angiogenesis-related biological events in the tissue or host, where the location of the radiolabeled γ-AApeptide corresponds to the location of the angiogenesis-related diseases or angiogenesis-related biological events.

In embodiments, the present disclosure also includes methods of inhibiting angiogenesis in a tissue or host by administering to the host or tissue an angiogenesis inhibitory amount of a γ-AApeptide compound capable of binding an RGD binding site on integrin $\alpha_v\beta_3$.

In embodiments of the methods of the present disclosure, the γ-AApeptide compound can include monomeric γ-AApeptides of Formula I, multimeric γ-AApeptide compounds including two or more γ-AApeptide units of Formula I joined together, and linear or cyclic γ-AApeptide compounds.

BRIEF DESCRIPTION OF THE DRAWINGS

Further aspects of the present disclosure will be more readily appreciated upon review of the detailed description of its various embodiments, described below, when taken in conjunction with the accompanying drawings.

FIG. 5A is a series of coronal and transaxial PET images of U87MG tumor-bearing mice at 0.5, 2, 4, and 24 h after injection of [64]Cu-γ-AA2, or co-injection of c(RGDyK) and [64]Cu-γ-AA2 (i.e., blocking). Arrowheads indicate tumors. FIGS. 5B and 5C are graphs of time-activity curves of the liver, tumor, blood, kidney, and muscle in U87MG tumor-bearing mice after injection of [64]Cu-γ-AA2 (5B), or co-injection of [64]Cu-γ-AA2 and a blocking dose of c(RGDyK) (5C). FIG. 5D is a bar graph showing a comparison of U87MG tumor uptake of [64]Cu-γ-AA2 between the two groups. FIG. 5E is a bar graph illustrating biodistribution data at 24 h post-injection of the tracer. *: $p<0.05$ (n=3)

DETAILED DESCRIPTION

Figure 1:
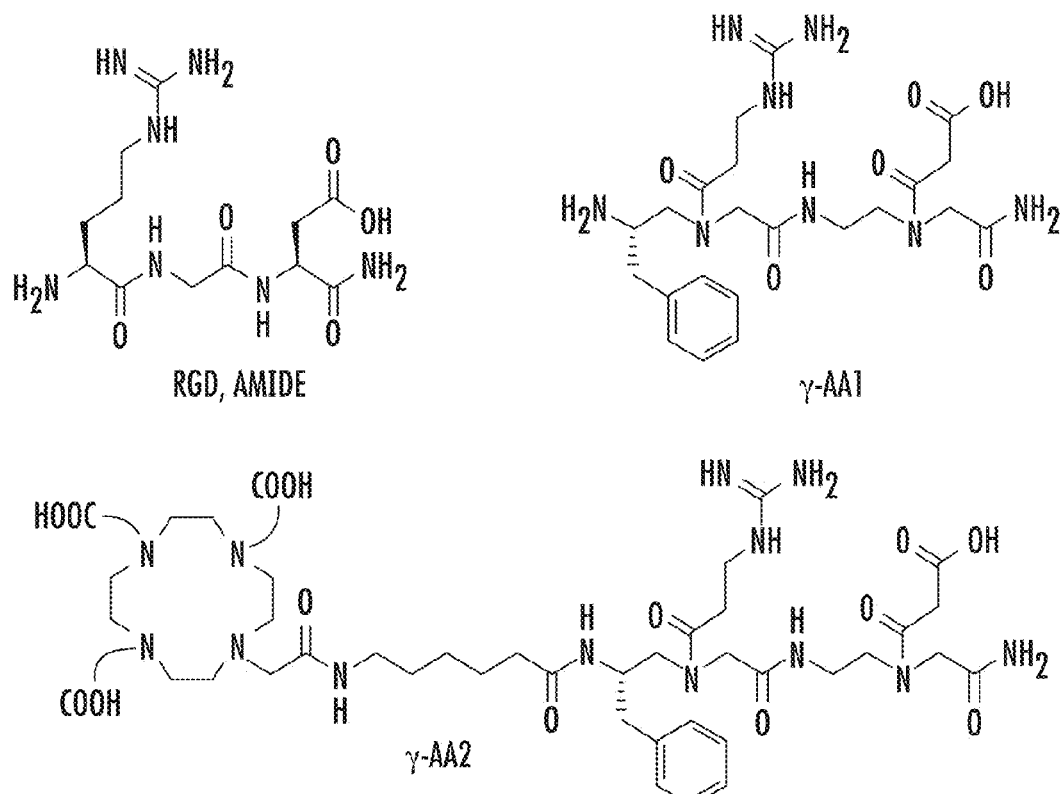
FIG. 1 illustrates the chemical structures of an RGD tripeptide and two representative γ-AApeptides of the present disclosure. γ-AA1 is a γ-AApeptide that mimics RGD, and γ-AA2 is a DOTA conjugated γ-AA1 useful for $^{64}$Cu-labeling and PET imaging.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

Any publications and patents cited in this specification that are incorporated by reference are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of organic chemistry, biochemistry, molecular biology, medicine, pharmacology, imaging, and the like, which are within the skill of the art. Such techniques are explained fully in the literature.

It must be noted that, as used in the specification and the appended embodiments, the singular forms "a," "an," and "the" include plural referents unless the context clearly dictates otherwise. Thus, for example, reference to "a cell" includes a plurality of cells. In this specification and in the embodiments that follow, reference will be made to a number of terms that shall be defined to have the following meanings unless a contrary intention is apparent.

Prior to describing the various embodiments, the following definitions are provided and should be used unless otherwise indicated.

DEFINITIONS

In describing the disclosed subject matter, the following terminology will be used in accordance with the definitions set forth below.

The terms "polypeptides" and "peptides" include proteins and fragments thereof. Polypeptides are disclosed herein as amino acid residue sequences. Those sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

"Variant" refers to a polypeptide or polynucleotide that differs from a reference polypeptide or polynucleotide, but retains essential properties. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more modifications (e.g., substitutions, additions, and/or deletions). A substituted or inserted amino acid residue may or may not be one encoded by the genetic code. A variant of a polypeptide may be naturally occurring such as an allelic variant, or it may be a variant that is not known to occur naturally.

Modifications and changes can be made in the structure of the polypeptides of this disclosure and still obtain a molecule having similar characteristics as the polypeptide (e.g., a conservative amino acid substitution). For example, certain amino acids can be substituted for other amino acids in a sequence without appreciable loss of activity. Because it is the interactive capacity and nature of a polypeptide that defines that polypeptide's biological functional activity, certain amino acid sequence substitutions can be made in a polypeptide sequence and nevertheless obtain a polypeptide with like properties.

In making such changes, the hydropathic index of amino acids can be considered. The importance of the hydropathic amino acid index in conferring interactive biologic function on a polypeptide is generally understood in the art. It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, such as enzymes, substrates, receptors, antibodies, antigens, and the like. It is known in the art that an amino acid can be substituted by another amino acid having a similar hydropathic index and still obtain a functionally equivalent polypeptide. In such changes, the substitution of amino acids whose hydropathic indices are within ±2 is preferred, those within ±1 are particularly preferred, and those within ±0.5 are even more particularly preferred. Substitution of like amino acids can also be made on the basis of hydrophilicity, particularly, where the biological functional equivalent polypeptide or peptide thereby created is intended for use in immunological embodiments. The following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent polypeptide. In such changes, the substitution of amino acids whose hydrophilicity values are within ±2 is preferred, those within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include (original residue: exemplary substitution): (Ala: Gly, Ser), (Arg: Lys), (Asn: Gln, His), (Asp: Glu, Cys, Ser), (Gln: Asn), (Glu: Asp), (Gly: Ala), (His: Asn, Gln), (Ile: Leu, Val), (Leu: Ile, Val), (Lys: Arg), (Met: Leu, Tyr), (Ser: Thr), (Thr: Ser), (Tip: Tyr), (Tyr: Trp, Phe), and (Val: Ile, Leu). Embodiments of this disclosure thus contemplate functional or biological equivalents of a polypeptide as set forth above. In particular, embodiments of the polypeptides can include variants having about 50%, 60%, 70%, 80%, 90%, and 95% sequence identity to the polypeptide of interest.

"Identity," as known in the art, is a relationship between two or more polypeptide sequences, as determined by comparing the sequences. In the art, "identity" also refers to the degree of sequence relatedness between polypeptide as determined by the match between strings of such sequences. "Identity" and "similarity" can be readily calculated by known methods, including, but not limited to, those described in Computational Molecular Biology, Lesk, A. M., Ed., Oxford University Press, New York, 1988; Biocomputing: Informatics and Genome Projects, Smith, D. W., Ed., Academic Press, New York, 1993; Computer Analysis of Sequence Data, Part I, Griffin, A. M., and Griffin, H. G., Eds., Humana Press, New Jersey, 1994; Sequence Analysis in Molecular Biology, von Heinje, G., Academic Press, 1987; and Sequence Analysis Primer, Gribskov, M. and Devereux, J., Eds., M Stockton Press, New York, 1991; and Carillo, H., and Lipman, D., SIAM J Applied Math., 48: 1073, (1988).

Preferred methods to determine identity are designed to give the largest match between the sequences tested. Methods to determine identity and similarity are codified in publicly available computer programs. The percent identity between two sequences can be determined by using analysis software (i.e., Sequence Analysis Software Package of the Genetics Computer Group, Madison Wis.) that incorporates the Needelman and Wunsch, (J. Mol. Biol., 48: 443-453, 1970) algorithm (e.g., NBLAST, and XBLAST). The default parameters are used to determine the identity for the polypeptides of the present disclosure.

By way of example, a polypeptide sequence may be identical to the reference sequence, that is be 100% identical, or it may include up to a certain integer number of amino acid alterations as compared to the reference sequence such that the % identity is less than 100%. Such alterations are selected from: at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence, or in one or more contiguous groups within the reference sequence. The number of amino acid alterations for a given % identity is determined by multiplying the total number of amino acids in the reference polypeptide by the numerical percent of the respective percent identity (divided by 100) and then subtracting that product from said total number of amino acids in the reference polypeptide.

Conservative amino acid variants can also comprise non-naturally occurring amino acid residues. Non-naturally occurring amino acids include, without limitation, trans-3-methylproline, 2,4-methanoproline, cis-4-hydroxyproline, trans-4-hydroxyproline, N-methyl-glycine, allo-threonine, methylthreonine, hydroxy-ethylcysteine, hydroxyethylhomocysteine, nitro-glutamine, homoglutamine, pipecolic acid, thiazolidine carboxylic acid, dehydroproline, 3- and 4-methylproline, 3,3-dimethylproline, tert-leucine, norvaline, 2-azaphenyl-alanine, 3-azaphenylalanine, 4-azaphenylalanine, and 4-fluorophenylalanine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is carried out in a cell-free system comprising an *E. coli* S30 extract and commercially available enzymes and other reagents. Proteins are purified by chromatography. (Robertson, et al., J. Am. Chem. Soc., 113: 2722, 1991; Ellman, et al., Methods Enzymol., 202: 301, 1991; Chung, et al., Science, 259: 806-9, 1993; and Chung, et al., Proc. Natl. Acad. Sci. USA, 90: 10145-9, 1993). In a second method, translation is carried out in *Xenopus oocytes* by microinjection of mutated mRNA and chemically aminoacylated suppressor tRNAs (Turcatti, et al., J. Biol. Chem., 271: 19991-8, 1996). Within a third method, *E. coli* cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the protein in place of its natural counterpart. (Koide, et al., Biochem., 33: 7470-6, 1994).

Naturally occurring amino acid residues can be converted to non-naturally occurring species by in vitro chemical modification. Chemical modification can be combined with site-directed mutagenesis to further expand the range of substitutions (Wynn, et al., Protein Sci., 2: 395-403, 1993).

As used herein, the term "peptidomimetics" refers to compounds having a protein-like chain that are designed to mimic peptides, but that have an altered chemistry that does not occur naturally, such as an altered backbone or the incorporation of non-natural amino acids.

The term "γ-AApeptide" refers herein to a class of peptidomimetic compounds having the backbone structure shown below (compared to a natural α peptide).

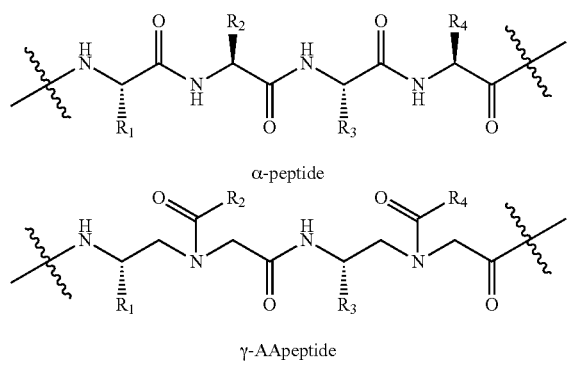

α-peptide

γ-AApeptide

The repeating unit of the γ-AApeptide backbone, as compared to two adjacent residues of an α-peptide, contains two side chains (including the R groups), one of which is an α-amino acid side chain, while the other comes from a carboxylic acid residue on the tertiary amide nitrogen. The term "γ-AApeptide compound" refers to compounds of the present disclosure including compounds having γ-AApeptide structure. For instance, embodiments of γ-AApeptide compounds of the present disclosure include compounds having the structure of Formula 1, below, as well as multimeric and/or cyclic compounds including one or more units having the structure of Formula 1 (e.g., "γ-AApeptide units").

As used herein, the term "detectable label", "imaging agent", or "imaging compound" refers to the labeled compounds of the present disclosure that are capable of serving as imaging agents and whose uptake is related to the expression level of certain surface cell receptors (e.g., integrin αvβ3). In particular non-limiting embodiments the imaging probes or imaging agents of the present disclosure are labeled with a PET isotope, such as F-18, Cu-64, and Ga-68.

By "administration" is meant introducing a compound of the present disclosure into a subject. The preferred route of administration of the compounds is intravenous. However, any route of administration, such as oral, topical, subcutaneous, peritoneal, intraarterial, inhalation, vaginal, rectal, nasal, introduction into the cerebrospinal fluid, or instillation into body compartments can be used.

In accordance with the present disclosure, "a detectably effective amount" of the imaging agent of the present disclosure is defined as an amount sufficient to yield an acceptable image using equipment that is available for clinical use. A detectably effective amount of the imaging agent of the present disclosure may be administered in more than one injection. The detectably effective amount of the imaging agent of the present disclosure can vary according to factors such as the degree of susceptibility of the individual, the age, sex, and weight of the individual, idiosyncratic responses of the individual, the dosimetry, and the like. Detectably effective amounts of the imaging agent of the present disclosure can also vary according to instrument and film-related factors. Optimization of such factors is well within the level of skill in the art. The term "therapeutically effective amount" as used herein refers to that amount of the compound being administered which will relieve to some extent one or more of the symptoms of a disease, a condition, or a disorder being treated. In reference to cancer or pathologies related to unregulated cell division, a therapeutically effective amount refers to that amount which has the effect of (1) reducing the size of a tumor, (2) inhibiting (that is, slowing to some extent, preferably stopping) aberrant cell division, for example cancer cell division, (3) preventing or reducing the metastasis of cancer cells, and/or, (4) relieving to some extent (or, preferably, eliminating) one or more symptoms associated with a pathology related to or caused in part by unregulated or aberrant cellular division, including for example, cancer, or angiogenesis.

"Treating" or "treatment" of a disease (or a condition or a disorder) includes preventing the disease from occurring in an animal that may be predisposed to the disease but does not yet experience or exhibit symptoms of the disease (prophylactic treatment), inhibiting the disease (slowing or arresting its development), providing relief from the symptoms or side-effects of the disease (including palliative treatment), and relieving the disease (causing regression of the disease). With regard to cancer, these terms also mean that the life expectancy of an individual affected with a cancer will be increased or that one or more of the symptoms of the disease will be reduced.

As used herein, the term "host" or "organism" includes humans, mammals (e.g., cats, dogs, horses, etc.), living cells, and other living organisms. A living organism can be as simple as, for example, a single eukaryotic cell or as complex as a mammal. Typical hosts to which embodiments of the present disclosure may be administered will be mammals, particularly primates, especially humans. For veterinary applications, a wide variety of subjects will be suitable, e.g., livestock such as cattle, sheep, goats, cows, swine, and the like; poultry such as chickens, ducks, geese, turkeys, and the like; and domesticated animals particularly pets such as dogs and cats. For diagnostic or research applications, a wide variety of mammals will be suitable subjects, including rodents (e.g., mice, rats, hamsters), rabbits, primates, and swine such as inbred pigs and the like. Additionally, for in vitro applications, such as in vitro diagnostic and research applications, body fluids and cell samples of the above subjects will be suitable for use, such as mammalian (particularly primate such as human) blood, urine, or tissue samples, or blood, urine, or tissue samples of the animals mentioned for veterinary applications. In some embodiments, a system includes a sample and a host. The term "living host" refers to host or organisms noted above that are alive and are not dead. The term "living host" refers to the entire host or organism and not just a part excised (e.g., a liver or other organ) from the living host.

The term "sample" can refer to a tissue sample, cell sample, a fluid sample, and the like. The sample may be taken from a host. The tissue sample can include hair (including roots), buccal swabs, blood, saliva, semen, muscle, or from any internal organs. The fluid may be, but is not limited to, urine, blood, ascites, pleural fluid, spinal fluid, and the like. The body tissue can include, but is not limited to, skin, muscle, endometrial, uterine, and cervical tissue. In the present disclosure, the source of the sample is not critical.

The term "detectable" refers to the ability to detect a signal over a background signal.

The term "detectable signal" is a signal derived from non-invasive imaging techniques such as, but not limited to, positron emission tomography (PET), single photon emission computed tomography (SPECT), optical imaging, magnetic resonance imaging (MRI), computer topography (CT), or ultrasound. The detectable signal is detectable and distinguishable from other background signals that may be generated from the host. In other words, there is a measurable and statistically significant difference (e.g., a statistically significant difference is enough of a difference to distinguish among the detectable signal and the background, such as about 0.1%, 1%, 3%, 5%, 10%, 15%, 20%, 25%, 30%, or 40% or more difference between the detectable signal and the background) between detectable signal and the background. Standards and/or calibration curves can be used to determine the relative intensity of the detectable signal and/or the background.

"Angiogenesis" is the physiological process involving the growth of new blood vessels. Excessive angiogenesis occurs when diseased cells produce abnormal amounts of angiogenic growth factors, overwhelming the effects of natural angiogenesis inhibitors. Imbalances between the production of angiogenic growth factors and angiogenesis inhibitors can cause improperly regulated growth or suppression of vascular vessels. Angiogenesis-dependent or related diseases result when new blood vessels either grow excessively or insufficiently. The angiogenesis related disease can include diseases such as, but not limited to, cancer, precancerous tissue, tumors, cardiac infarction, and stroke. Excessive angiogenesis can include: cancer, diabetic blindness, age-related macular degeneration, rheumatoid arthritis, psoriasis, and more than 70 other conditions. Insufficient angiogenesis can include: coronary artery disease, stroke, and delayed wound healing. In particular, angiogenesis related disease includes diseases and conditions including or relating to the vitronectic receptor integrin αvβ3. Additional details regarding integrin $\alpha_v\beta_3$ are described in the Examples.

"Cancer", as used herein, shall be given its ordinary meaning, as a general term for diseases in which abnormal cells divide without control. In particular, cancer refers to angiogenesis related cancer. Cancer cells can invade nearby tissues and can spread through the bloodstream and lymphatic system to other parts of the body. There are several main types of cancer, for example, carcinoma is cancer that begins in the skin or in tissues that line or cover internal organs. Sarcoma is cancer that begins in bone, cartilage, fat, muscle, blood vessels, or other connective or supportive tissue. Leukemia is cancer that starts in blood-forming tissue such as the bone marrow, and causes large numbers of abnormal blood cells to be produced and enter the bloodstream. Lymphoma is cancer that begins in the cells of the immune system. When normal cells lose their ability to behave as a specified, controlled and coordinated unit, a tumor is formed. Generally, a solid tumor is an abnormal mass of tissue that usually does not contain cysts or liquid areas (some brain tumors do have cysts and central necrotic areas filled with liquid). A single tumor may even have different populations of cells within it, with differing processes that have gone awry. Solid tumors may be benign (not cancerous), or malignant (cancerous). Different types of solid tumors are named for the type of cells that form them. Examples of solid tumors are sarcomas, carcinomas, and lymphomas. Leukemias (cancers of the blood) generally do not form solid tumors.

Representative cancers include, but are not limited to, bladder cancer, breast cancer, colorectal cancer, endometrial cancer, head and neck cancer, leukemia, lung cancer, lymphoma, melanoma, non-small-cell lung cancer, ovarian cancer, prostate cancer, testicular cancer, uterine cancer, cervical cancer, thyroid cancer, gastric cancer, brain stem glioma, cerebellar astrocytoma, cerebral astrocytoma, glioblastoma, ependymoma, Ewing's sarcoma family of tumors, germ cell tumor, extracranial cancer, Hodgkin's disease, leukemia, acute lymphoblastic leukemia, acute myeloid leukemia, liver cancer, medulloblastoma, neuroblastoma, brain tumors generally, non-Hodgkin's lymphoma, osteosarcoma, malignant fibrous histiocytoma of bone, retinoblastoma, rhabdomyosarcoma, soft tissue sarcomas generally, supratentorial primitive neuroectodermal and pineal tumors, visual pathway and hypothalamic glioma, Wilms' tumor, acute lymphocytic leukemia, adult acute myeloid leukemia, adult non-Hodgkin's lymphoma, chronic lymphocytic leukemia, chronic myeloid leukemia, esophageal cancer, hairy cell leukemia, kidney cancer, multiple myeloma, oral cancer, pancreatic cancer, primary central nervous system lymphoma, skin cancer, small-cell lung cancer, among others.

A tumor can be classified as malignant or benign. In both cases, there is an abnormal aggregation and proliferation of cells. In the case of a malignant tumor, these cells behave more aggressively, acquiring properties of increased invasiveness. Ultimately, the tumor cells may even gain the ability to break away from the microscopic environment in which they originated, spread to another area of the body (with a very different environment, not normally conducive to their growth), and continue their rapid growth and division in this new location. This is called metastasis. Once malignant cells have metastasized, achieving a cure is more difficult.

It should be noted that precancerous cells, cancer, and tumors are often used interchangeably in the disclosure.

General Discussion:

The present disclosure provides novel peptidomimetics, including γ-AApeptides, capable of binding to an RGD binding site, such as in integrin $\alpha_v\beta_3$, methods of using the γ-AApeptides, and methods of making the γ-AApeptides. As described above, it would be desirable to have a labeled RGD ligand that is stable and resistant to proteolytic degradation to detect a physiological condition, such as cancer. Described herein are embodiments of γ-AApeptides, pharmaceutical compositions including the γ-AApeptides, imaging compounds including the γ-AApeptides, methods of using the γ-AApeptides to detect cancer, and therapeutic methods using the γ-AApeptides. In the following disclosure, various specific embodiments are described. It is to be understood that those embodiments are example implementations of the disclosed inventions and that alternative embodiments are possible. All such embodiments are intended to fall within the scope of this disclosure.

Since integrin $\alpha_v\beta_3$ binds tightly to extracellular matrix proteins that contain the Arg-Gly-Asp (RGD) tripeptide epitopes, a wide variety of peptides/peptidomimetics based on the RGD motif have been investigated for anti-cancer drug development and/or cancer imaging.[5a, 6] However, peptide based RGD mimetics suffer from intrinsic poor stability against proteolytic degradation.[21, 22] Linear RGD peptides are degraded in minutes. While cyclization increased the stability against enzymatic degradation, they are still hydrolyzed in hours, even when unnatural D-amino acids are introduced into the rings. Such disadvantages pose obstacles for their further development for cancer therapeutics or targeted imaging. As for the small non-peptidic molecules,[23] they either lack specificity or are difficult to derivatize for application (e.g., attachment of radioisotopes or fluorophores for targeted imaging). As such, there is a need for the further development of RGD mimetics that can recognize integrin $\alpha_v\beta_3$ with increased stability, affinity, and specificity in both in vitro and in vivo, to facilitate the development of novel anti-cancer therapeutics and diagnostics.

The present disclosure provides alternative compounds to traditional RGD peptides, including a new family of protease-resistant peptidomimetics (γ-AApeptides).[24-26] As demonstrated in the Example below, the γ-AApeptides of the present disclosure show the capability to recognize $\alpha_v\beta_3$ with affinity and specificity comparable to c(RGDyK), a most commonly used cyclic RGD pentapeptide for tumor targeted imaging, but they also possess significantly enhanced stability. Additionally, the design and synthesis of these compounds is relatively straightforward, allowing for extensive derivatization to enhance activity. As such, these γ-AApeptides represent novel RGD mimetics that can recognize integrin $\alpha_v\beta_3$ with enhanced stability and activity and can be used to develop new agents for targeted therapy and diagnosis of conditions and cancers, such as but not limited to glioblastoma.

The γ-AApeptides of the present disclosure can also lead to development of additional γ-AApeptides and other classes of peptidomimetics to target other integrin sub-types involved in many other important biological processes. Furthermore, this research can advance the peptidomimetic field within biomedical sciences As such, embodiments of the present disclosure include a new class of γ-AApeptide based RGD mimetics as novel anti-angiogenic agents for cancer targeted diagnosis, prevention, and therapy. Embodiments of the present disclosure also include novel γ-AApeptide based RGD mimetics specifically targeting integrin $\alpha_v\beta_3$ in both in vitro and in vivo in a glioblastoma tumor model. In embodiments of the present disclosure, γ-AApeptides containing guanidino and carboxylic groups with a spatial relationship similar to that in RGD peptide are provided that are able to mimic the functional motif of RGD. Embodiments of the present disclosure include linear γ-AApeptides, cyclic γ-AApeptides, and multimeric linear and cyclic γ-AApeptides that can mimic the structural and functional motif of RGD. In embodiments, such γ-AApeptides of the present disclosure specifically recognize integrin $\alpha_v\beta_3$ and have binding activity comparable or better than the positive control c(RGDyK), while exhibiting better stability and resistance to proteolysis.

The example below further describes the synthesis of the γ-AApeptides of the present disclosure, the structure-activity relationship existing in γ-AApeptides for the recognition of integrin $\alpha_v\beta_3$, and identifies representative embodiments of γ-AApeptides that can bind to $\alpha_v\beta_3$ with high specificity and affinity in glioblastoma tumor cells and in a glioblastoma tumor-inoculated mice model. The results of the studies described in the examples not only introduces a new class of RGD mimetics, but also describes compounds that can lead to novel anticancer agents for targeted drug delivery, diagnosis and treatment cancers including, but not limited to, glioblastoma. As overexpression of $\alpha_v\beta_3$ is also identified in other tumors, the γ-AApeptide based RGD mimetics have great potential as anti-cancer agents to treat many other cancers such as lung cancer, breast cancer and prostate cancer, etc.

Angiogenesis and Integrins.

Angiogenesis is an emerging target for diagnostic imaging and drug therapy because of its key role in tumor growth.[17, 32-35] One very promising anti-angiogenic approach is to develop agents that can specifically target integrins. Each integrin molecule includes one α subunit and one β subunit, which are non-covalently associated together. Currently, 18 α and 8 β subunits have been identified with the ability to assemble into at least 24 different heterodimers mediating cell adhesions.[23, 39] Since many of these are critical for tumor angiogenesis,[40, 41] they have been identified as active targets for anti-angiogenic development.[5-8] As discussed above, integrin $\alpha_v\beta_3$ is closely involved in angiogenesis and metastasis of glioblastoma tumor and many other solid tumors.[9, 10] As such, molecules specifically targeting this type of integrin are promising anti-cancer agents for both diagnosis and treatment of glioblastoma cancer and other cancers.

Peptide-Based RGD Mimetics.

Significant interest exists in the development of molecules including peptides and non-peptidic small molecules that can mimic RGD motif and specifically target integrins for cancer targeted imaging and cancer treatment.[18, 20, 23, 39, 42-59] The structures of a few common RGD-motif-containing peptide analogues are shown below.

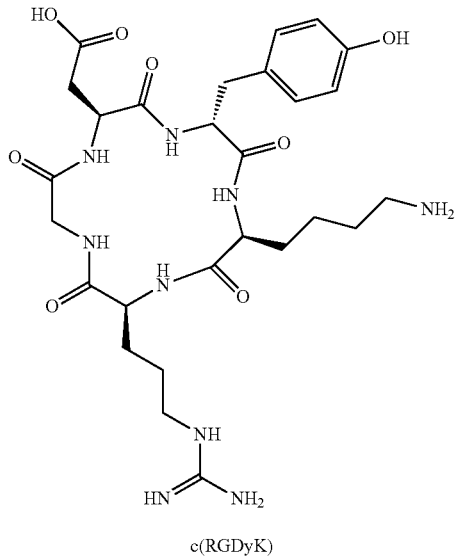

c(RGDyK)

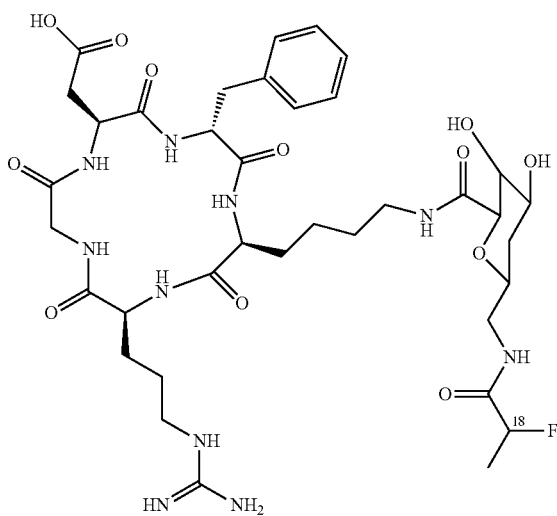

[$^{18}$F-galacto]-c(RGDfK)

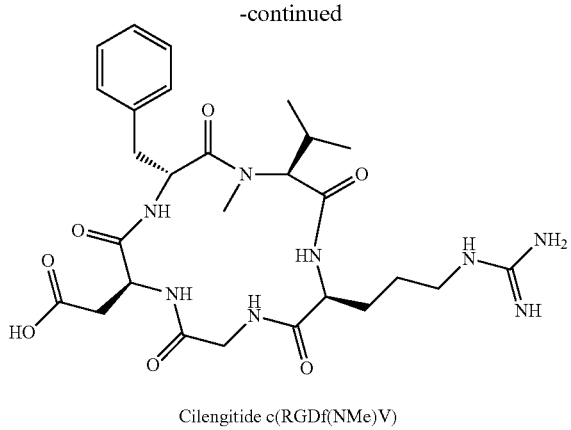

Cilengitide c(RGDf(NMe)V)

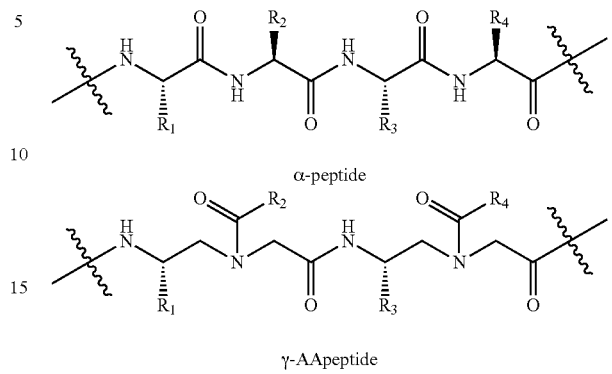

α-peptide

γ-AApeptide

For example cyclo-(Arg-Gly-Asp-$_D$-Tyr-Lys), referred as c(RGDyK) (shown below), which specifically targets integrin $\alpha_v\beta_3$, has been extensively used for tumor targeted drug delivery, therapy, and nuclear and optical imaging applications,[53, 54, 60-64] including glioblastoma cancer targeted imaging in mouse model.[65, 66] Another $^{18}$F-labeled RGD peptide derivative, [$^{18}$F-galacto]-c(RGDfK), is under clinical investigation for the identification of $\alpha_v\beta_3$ receptor expression in patents in glioblastoma cancer and a few other cancer types.[67-69] Cilengitide, c(RGDf(NMe)V), which binds integrin $\alpha_v\beta_3$ with subnanomolar activity, is the first anti-angiogenic small molecule drug candidate currently in clinical phase III for the treatment of glioblastomas, and in phase II for non-small cell lung cancer[10, 43] as well as a few other solid tumors. It is now widely accepted that molecules containing multimeric RGD peptide motif will increase the binding affinity and specificity towards integrins.[50, 52, 59, 70-75]

However, peptide-based RGD mimetics suffer from intrinsic poor stability against proteolytic degradation.[21, 22] Linear RGD peptides are degraded in minutes, while cyclized peptides are still hydrolyzed in hours, even when unnatural D-amino acids are introduced. Such disadvantages pose obstacles for further development of RGD peptides. As for some small non-peptidic molecules, they either lack specificity or are difficult to derivatize for application (e.g., attachment of radioisotopes, fluorophores, or drugs for targeted imaging and drug delivery). Thus, in order to specifically target integrin $\alpha_v\beta_3$ to facilitate cancer targeted imaging and treatment, the further development of more stable RGD mimetics is needed.

γ-AApeptides

The compounds of the present disclosure represent a new class of oligomeric peptidomimetics, termed "γ-AApeptides". The γ-AApeptides of the present disclosure have the basic, backbone structure shown below alongside the structure of the naturally occurring α-peptides.[76]

Compared to natural α-peptides, the repeating unit of the γ-AApeptide backbone contains two side chains, one of which is an α-amino acid side chain, while the other comes from a carboxylic acid residue on the tertiary amide nitrogen. As such, γ-AApeptides can project an identical number of side functional groups as conventional peptides of the same length. Such γ-AApeptides are designed so that they can be efficiently synthesized and easily derivatized, while potentially keeping the structural and functional properties of conventional peptides. Since half of side chains can come from any carboxylic acids, there is great potential for generating chemically diverse γ-AApeptide libraries.

γ-AApeptides can effectively disrupt p53-MDM2 protein-protein interactions,[76] and recognize HIV RNA with an affinity and specificity similar to HIV Tat peptide.[77] γ-AApeptides have also been demonstrated as potent and broad-spectrum antimicrobial peptidomimetics to circumvent drug resistance.[78] More importantly, γ-AApeptides are highly resistant to protease degradation, augmenting their potential applications in biological sciences.[76] γ-AApeptides were used to develop RGD mimetics with enhanced stability and activity towards integrin $\alpha_v\beta_3$ so as to develop novel anti-angiogenic agents for early diagnosis, prevention, and treatment of cancer, as described in greater detail in the Example below.

Design and Synthesis of γ-AApeptides Mimicking RGD Motif.

Embodiments of the present disclosure include linear and cyclic γ-AApeptide derivatives that can mimic the RGD peptide motif, including but not limited to, the embodiments of γ-AApeptides of the present disclosure having the structures γ-AA2 to γ-AA7, below.

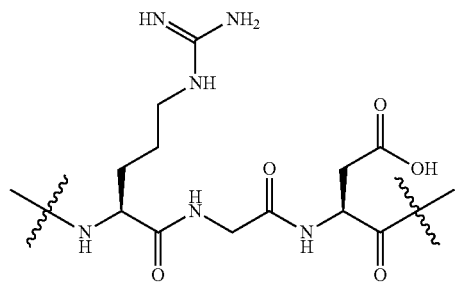

RGD

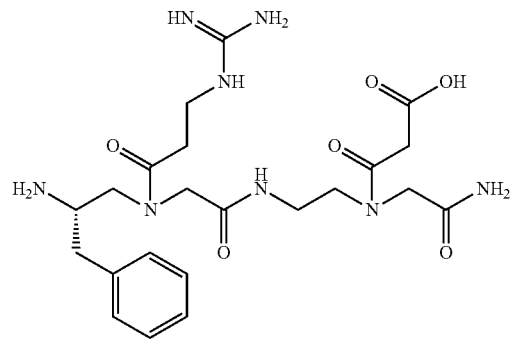

γ-AA2

-continued
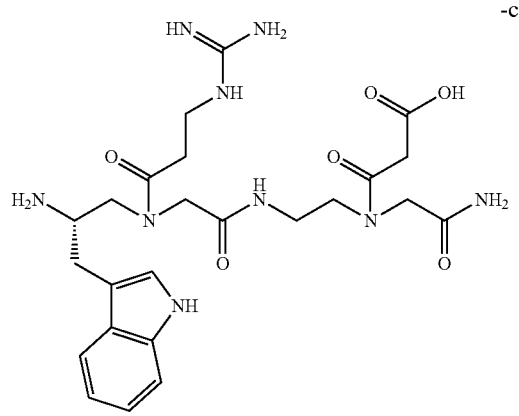
γ-AA4
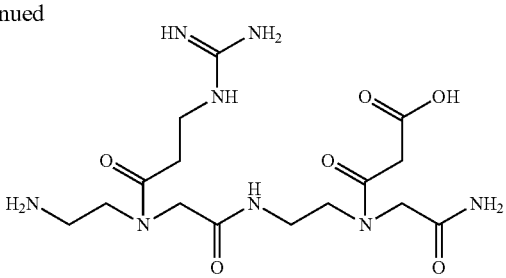
γ-AA1
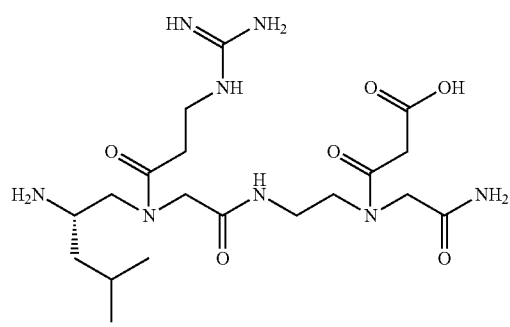
γ-AA3
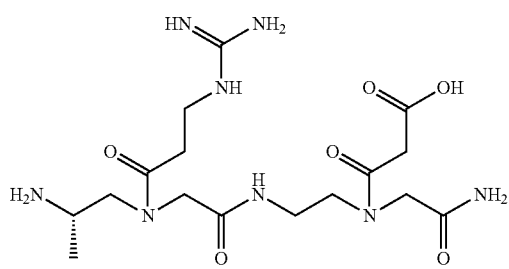
γ-AA5
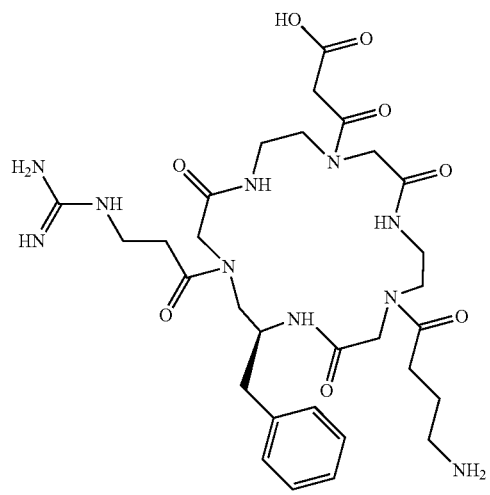
γ-AA6

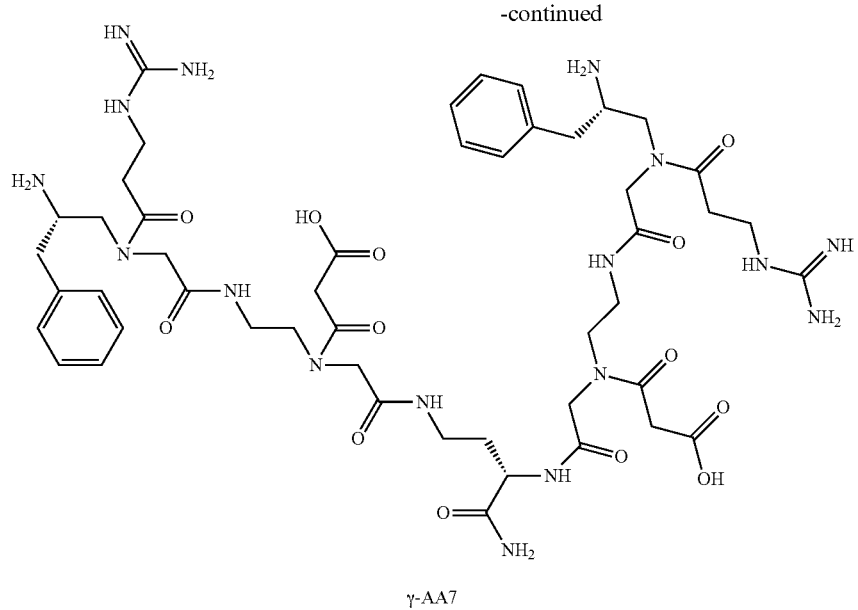

γ-AA7

γ-AApeptides can project virtually any functional groups through acylation, and they can contain the same number of functional groups as peptides of same lengths.[76-78] As shown above, the spatial distance of positively charged guanidino group and carboxyl group in the γ-AApeptide is similar to the distance between side chains of Arg and Asp residues in the RGD peptide. Other functional groups, such as phenyl (γ-AA2), isopropyl groups (γ-AA3), indole group (γ-AA4), methyl group (γ-AA5) are introduced next to the RGD-mimicking fragment to fine tune the activity and selectivity. γ-AA1 is an embodiment of a linear RGD mimetic that does not possess the extra side chain. Since it is reported that cyclic RGD peptides are more selective and potent than linear RGD peptides,[11, 15] and multimeric RGD peptides have higher binding affinity towards integrins,[11, 15] a cyclic γ-AApeptide RGD mimetic (γ-AA6) and a dimeric γ-AApeptide RGD mimetic (γ-AA7) were also prepared so as to compare their binding affinity and selectivity towards their linear γ-AApeptide counterparts. The synthesis of linear and cyclic γ-AApeptides is possible on solid phase using either a building block strategy[25, 26, 78] or a step-by-step strategy described in Example 1 below.

Additional details regarding the γ-AApeptides of the present disclosure and methods of making and using the compounds of the present disclosure can be found in the Examples below.

In embodiments, the linear γ-AApeptides of the present disclosure that mimic RGD peptides have the structure shown in Formula I, below. R1, R2 and R3 can be chosen from various moieties tailored to the desired function of the γ-AApeptides, and can have various chemical structures so long as they do not impede the function of the γ-AApeptides. In embodiments, the R1 group may be a hydrophobic moiety, a charged moiety, a polar moiety, or a neutral moiety. In some embodiments, R1 is selected from one of the moieties shown below. In embodiments R2 and R3 are selected from one of the group of moieties shown below.

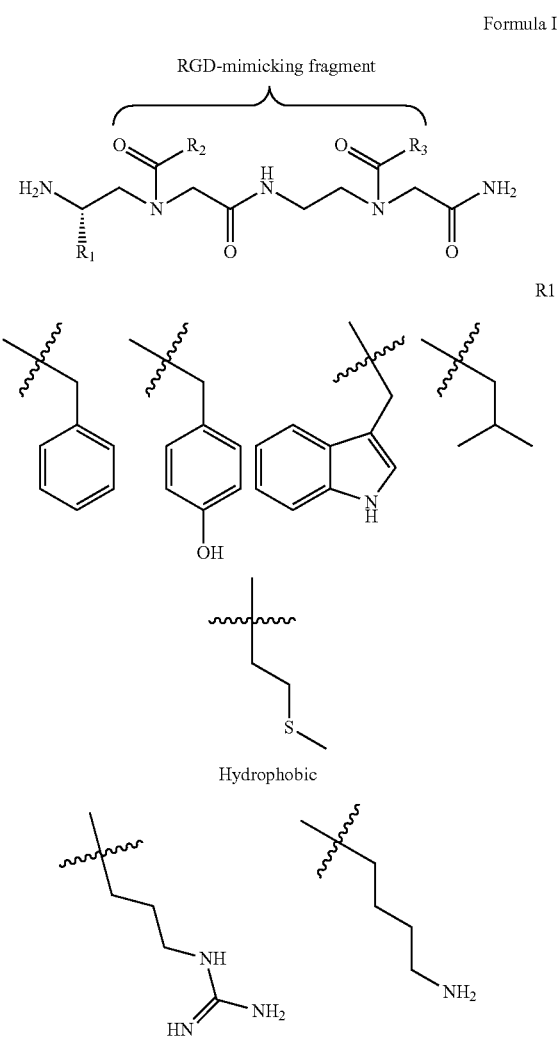

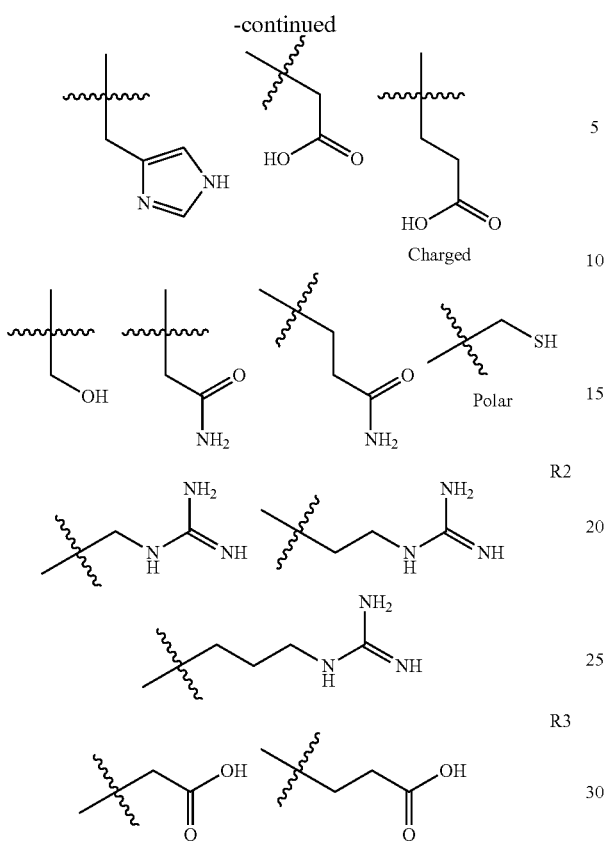

Charged

Polar

R2

R3

Traditional, linear RGD peptides could not be extensively used because they are susceptible to quick enzymatic degradation and lack potency and specificity.[92] However, based on the results shown in Example 1 below, these obstacles can be overcome by the linear γ-AApeptides of the present disclosure, which demonstrated greater stability as well as substantial potency and specificity.

The γ-AApeptide compounds of the present disclosure can include one or more γ-AApeptide units having the structure of Formula I. Additionally, it will be understood that Formula I can be extended so that the γ-AApeptide backbone continues and additional R groups are included (e.g., R4, R5, and so on). Additionally, variants of Formula I are included in the present disclosure, where the γ-AApeptide is cyclized (with the ends joined directly or via a linker).

As described in greater detail in Example 2 below, cyclic and multimeric γ-AApeptides that mimic RGD peptides are also included in the present disclosure. In embodiments, multimeric γ-AApeptides of the present disclosure include two or more γ-AApeptides joined by a linker. In embodiments, dimeric γ-AApeptides of the present disclosure have the following structure, where "γ-AApeptide" is a γ-AApeptide of the present disclosure, e.g., a γ-AApeptide of Formula I.

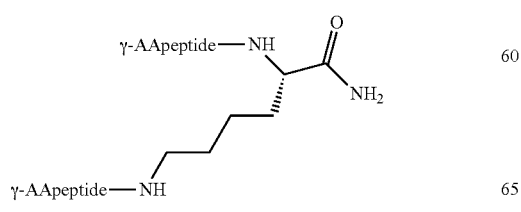

In additional embodiments, multimeric γ-AApeptides of the present disclosure include a tetrameric γ-AApeptide having two or more γ-AApeptides joined by one or more linkers. In an embodiment, a tetrameric γ-AApeptide of the present disclosure has the following structure, where "γ-AApeptide" is a γ-AApeptide unit of the present disclosure, e.g., a γ-AApeptide of Formula I.

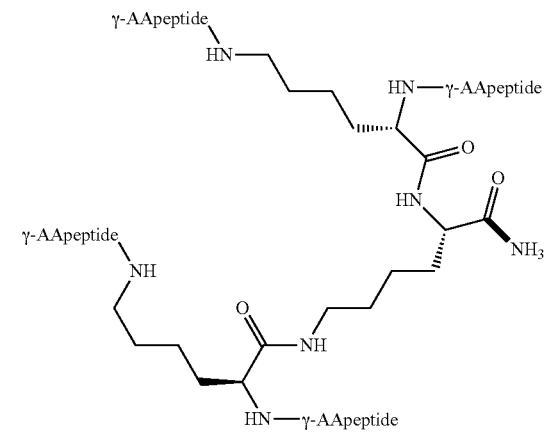

In embodiments of the present disclosure, cyclic γ-AApeptides of the present disclosure have the following structure, where R1, R2, and R3 can be as defined for Formula I above.

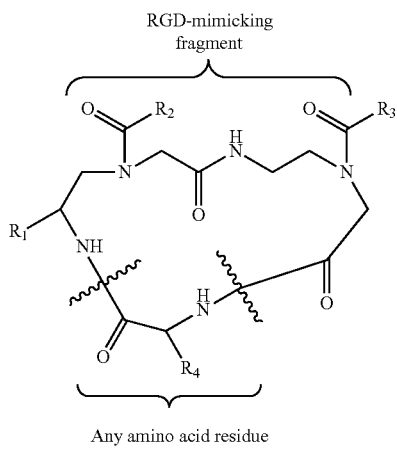

Any amino acid residue cyclic pentapeptide mimetics

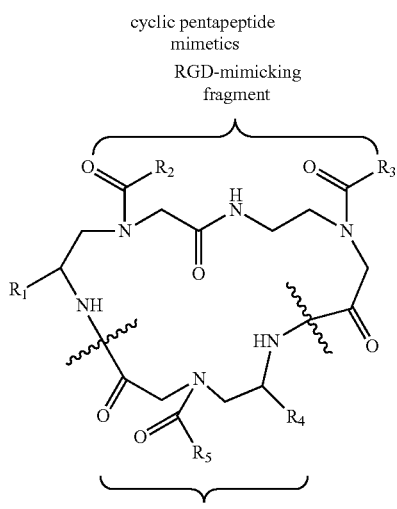

Any γ-AApeptide building block residue cyclic hexapeptide mimetics

Embodiments of the present disclosure also include pharmaceutical compositions including the γ-AApeptides, as salt, solvate or hydrate thereof, and a pharmaceutically acceptable carrier. The present disclosure also provides labeled γ-AApeptides, where the γ-AApeptides are coupled to a detectable label. The present disclosure also includes pharmaceutical compositions including a detectably effective amount of labeled γ-AApeptides of the present disclosure, where the label is capable of being detected by an imaging device, such as a positron emission technology imaging apparatus (e.g., a PET scanner). In embodiments, the label is a radiolabel capable of detection by a PET scanning device. In embodiments the radiolabel is conjugated by a chelating agent such as, but not limited to, DOTA (1,4,7,10-tetraazacyclododecane-1,4,7,10-tetraacetic acid $(CH_2CH_2NCH_2CO_2H)_4$) and NOTA (1,4,7-triazacyclononane-N,N',N''-triacetic acid $(CH_2CH_2NCH_2CO_2H)_3$). In embodiments, the label is $^{64}Cu$; in embodiments the γ-AApeptide is conjugated with DOTA or NOTA and labeled with $^{64}Cu$. The present disclosure also includes kits containing the γ-AApeptide compounds of the present disclosure coupled to a detectable label and including instructions for use of the labeled γ-AApeptide compounds.

Methods of making specific embodiments of the γ-AApeptides, including linear, cyclic and multimeric γ-AApeptides of the present disclosure and methods of making the detectably labeled γ-AApeptide are provided in the Examples. These specific methods can be generally applied to other compounds described herein.

Methods of Using RGD Mimetic γ-AApeptides.

The present disclosure also includes methods of detecting and/or imaging integrin $α_vβ_3$ by administering to a host or a tissue a detectably effective amount of a labeled γ-AApeptide of the present disclosure, where the labeled γ-AApeptide is capable of binding integrin $α_vβ_3$, and employing an imaging technology capable of detecting distribution of the labeled γ-AApeptide within the tissue and/or body or a portion thereof of the host. Detection of the distribution of the labeled γ-AApeptide indicates the presence and/or location of integrin $α_vβ_3$ in the host or tissue.

In embodiments, the imaging technology is a PET scanner. Since integrin $α_vβ_3$ is implicated in the angiogenesis pathway, in embodiments, the present disclosure also includes methods of imaging angiogenesis by administering to a host or a tissue a detectably effective amount of a labeled γ-AApeptide of the present disclosure, where the labeled γ-AApeptide is capable of binding integrin $α_vβ_3$, and employing an imaging technology capable of detecting distribution of the labeled γ-AApeptide within the tissue and/or body or a portion thereof of the host. Detection of the labeled γ-AApeptide indicates the occurrence/location of angiogenesis in the host or tissue. Detection of angiogenesis in the host or tissue can also indicate the presence of one or more angiogenesis-related diseases or angiogenesis-related biological events. Thus, methods of the present disclosure also include methods of detecting, imagining and/or diagnosing angiogenesis-related conditions and/or events (e.g., cancer, etc.).

Since the RGD mimetic γ-AApeptide compounds of the present disclosure bind to and can inhibit integrin $α_vβ_3$, the present disclosure also includes methods of inhibiting angiogenesis and/or disorders associated with angiogenesis (e.g., cancer, metastatic cancer, macular degeneration, etc.) in a tissue or a host by administering to a host in need thereof an angiogenesis inhibitory amount of a γ-AApeptide of the present disclosure to the host or the tissue.

The specific examples below are to be construed as merely illustrative, and not limitative of the remainder of the disclosure in any way whatsoever. Without further elaboration, it is believed that one skilled in the art can, based on the description herein, utilize the present disclosure to its fullest extent. All publications recited herein are hereby incorporated by reference in their entirety.

It should be emphasized that the embodiments of the present disclosure, particularly, any "preferred" embodiments, are merely possible examples of the implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure, and protected by the following embodiments.

The following examples are put forth so as to provide those of ordinary skill in the art with a complete disclosure and description of how to perform the methods and use the compositions and compounds disclosed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

In regard to the discussion herein, including the Examples below and the claims, it should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figures of the numerical value.

EXAMPLES

Now having described the embodiments of the present disclosure, in general, the following Examples describe some additional embodiments of the present disclosure. While embodiments of the present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure.

Example 1

Introduction

A γ-AApeptide-based tracer for positron emission tomography imaging of integrin $α_vβ_3$ expression in an animal tumor model is reported in this Example. With comparable integrin $α_vβ_3$ binding affinity as the cyclic arginine-glycine-aspartic acid (RGD) peptide but significantly higher resistance to enzymatic degradation (hence better in vivo stability), and despite its shorter sequence and linear nature, γ-AApeptide-based agents represent a new class of cancer imaging probes and/or therapeutics.

Figure 2:
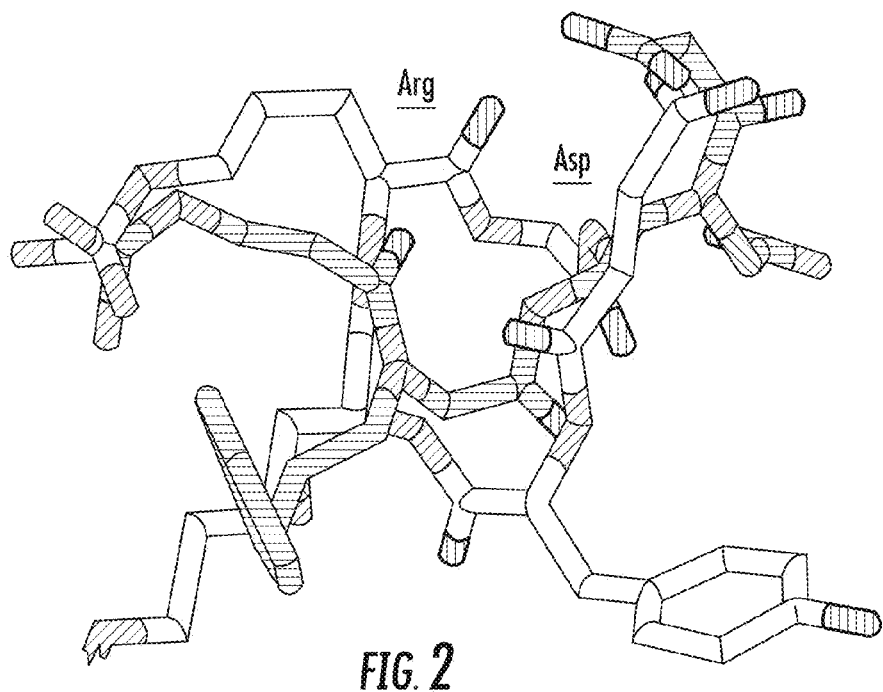
FIG. 2 is an illustration of the superimposed structures of energy-minimized γ-AA1 (horizontal hash marks) and c(RGDyK) (no hash marks). The energy minimization and superimposition was carried out using the ChemBioOffice program.

Discussion and Results:

This new class of peptidomimetics are termed "γ-AApeptides"[8] and have shown promising potential for various biological applications such as effective disruption of protein-protein interactions,[8] recognition of specific nucleic acids,[9] and as novel antimicrobial agents.[10] In addition, these γ-AApeptides are resistant to proteolytic degradation and are amenable for limitless diversification. Since γ-AApeptides can be designed to project the same number of side chains as that of peptides of the same length, they are good candidates for short peptide mimicry. To further explore their potential applications in biomedical research, and to develop novel molecular imaging agents, the present example describes development of short and linear γ-AApeptide-based RGD mimetics (FIG. 1), which can be employed for in vivo PET imaging of integrin $\alpha_v\beta_3$ expression. These results demonstrate that this new class of RGD mimetics have comparable integrin $\alpha_v\beta_3$ binding affinity and specificity to the commonly used c(RGDyK) (where y denotes D-tyrosine). Furthermore, they are much more protease-resistant, and hence are more suitable for PET imaging applications.

γ-AA1 is a γ-AApeptide designed to mimic the tripeptide RGD. An additional phenyl moiety was included in the molecule to provide a balance of hydrophilicity and hydrophobicity, as was found in other RGD-containing peptides for imaging and/or therapeutic applications,[6] which is not expected to interfere with integrin $\alpha_v\beta_3$ binding. To rationalize such design, structural studies were carried out by superimposing the energy-minimized structure of γ-AA1 onto that of c(RGDyK). As shown in FIG. 2, the guanidino and carboxyl groups within γ-AA1 superimpose very well with the functional groups of Arg and Asp residues from c(RGDyK), which are responsible for the recognition of integrin $\alpha_v\beta_3$. Thus, computer modeling supports the design of γ-AApeptides for RGD motif mimicry. Future systematic studies will be carried out to investigate the effect of different functional groups on integrin $\alpha_v\beta_3$ binding of the γ-AApeptide-based RGD mimetics.

Figure 3A:
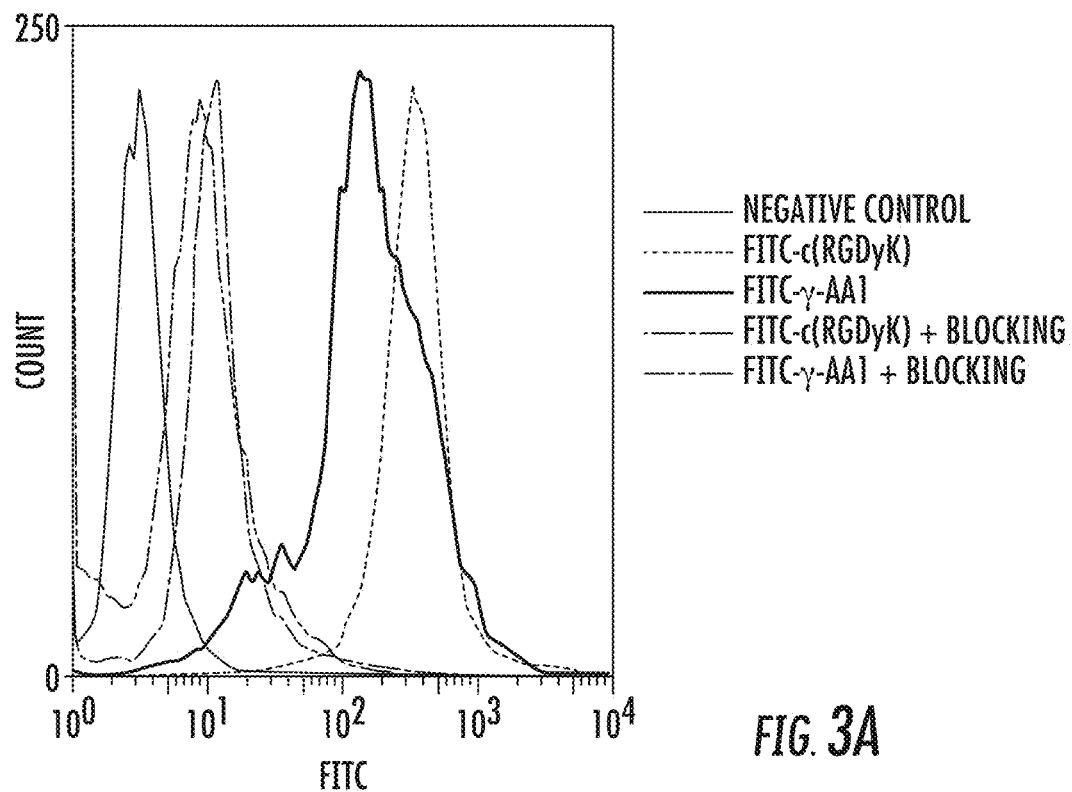
FIG. 3A is a graph illustrating flow cytometry analysis of FITC-conjugated γ-AA1 and c(RGDyK) peptide in U87MG cells at a 5 μg/mL concentration. Blocking experiments with 2 μM of c(RGDyK) peptide were also performed to confirm the specificity for integrin $\alpha_v\beta_3$.
Figure 3B:
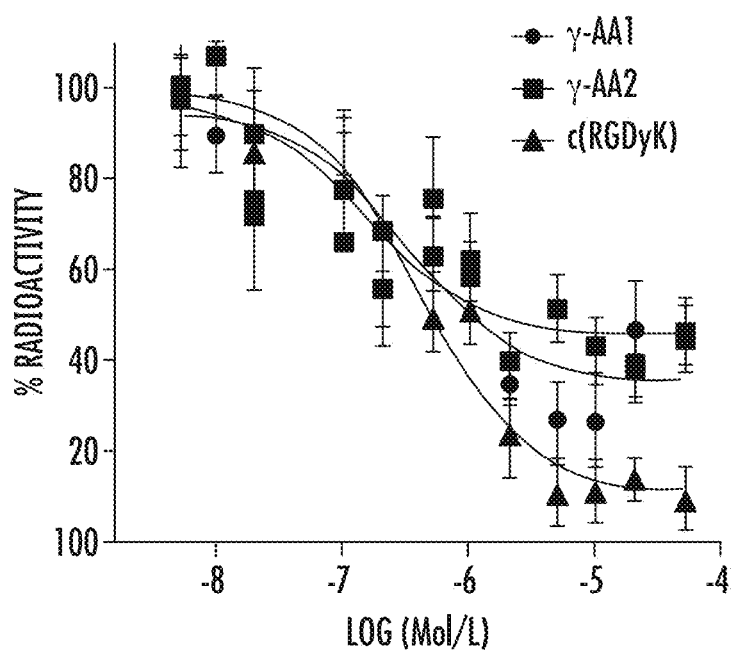
FIG. 3B is a graph illustrating a U87MG cell binding assay demonstrating that both γ-AA1 and γ-AA2 bind to integrin $\alpha_v\beta_3$, similar to the c(RGDyK) peptide.

To further evaluate the capability of the γ-AApeptides for RGD mimicry, γ-AA1 and the c(RGDyK) peptide, an extensively studied and validated high affinity antagonist for integrin $\alpha_v\beta_3$,[5a] were each conjugated to FITC. After purification by high performance liquid chromatography (HPLC), FITC-γ-AA1 and FITC-c(RGDyK) were compared for integrin $\alpha_v\beta_3$ binding affinity and specificity in U87MG human glioblastoma cells that express high level of integrin $\alpha_v\beta_3$.[11] At a 5 µg/mL concentration, which is under a non-saturating condition (i.e. the fluorescence signal was in the $10^2$-$10^3$ range instead of $10^4$), FITC-γ-AA1 has similar uptake in the U87MG cells as FITC-c(RGDyK), as evidenced by flow cytometry (FIG. 3a). Blocking the receptor with 2 µM of unconjugated c(RGDyK) significantly reduced the uptake of both FITC-γ-AA1 and FITC-c(RGDyK) to a similar extent. U87MG cell binding assay using $^{64}$Cu-DOTA-c(RGDyK) as the radioligand revealed that the $IC_{50}$ values were 831 and 897 nM for γ-AA1 and γ-AA2, respectively (FIG. 3b). These values are slightly lower but comparable to that of c(RGDyK), with an $IC_{50}$ value of 639 nM in the same assay. Together, these findings indicated that γ-AA1/γ-AA2 and the c(RGDyK) peptide have similar binding affinity and specificity to integrin $\alpha_v\beta_3$ in vitro.

To enable $^{64}$Cu-labeling and PET imaging, DOTA (1, 4, 7, 10-tetraazacyclododecane-1,4,7,10-tetraacetic acid) was linked to γ-AA1 via a 6-aminohexanoic acid linker, which was termed γ-AA2 DOTA-γ-AA1, FIG. 1). $^{64}$Cu-labeling of γ-AA2, including final purification with HPLC, took 90±15 min (n=8). The decay-corrected radiochemical yield was 50±15%, based on 2 µg of γ-AA2 per 37 MBq of $^{64}$Cu, with a radiochemical purity of >95%. The specific activity of $^{64}$Cu-γ-AA2 was measured to be ~9 GBq/mg of γ-AA2. The c(RGDyK) peptide was conjugated with DOTA, purified by HPLC, and labeled with $^{64}$Cu in a similar manner.

Before PET imaging was carried out to evaluate the in vivo behaviour of $^{64}$Cu-labeled γ-AA2, enzymatic stability of the tracer was investigated. Pronase, a mixture of proteinases isolated from the extracellular fluid of *Streptomyces griseus*, was used to compare the enzymatic stability of the two PET tracers.[8, 12] After incubation with 0.1 mg/mL of pronase at 37° C. in 100 mM ammonium bicarbonate buffer (pH 7.8) for various time periods, stability of the two tracers was compared using radio-HPLC.

Figure 4:
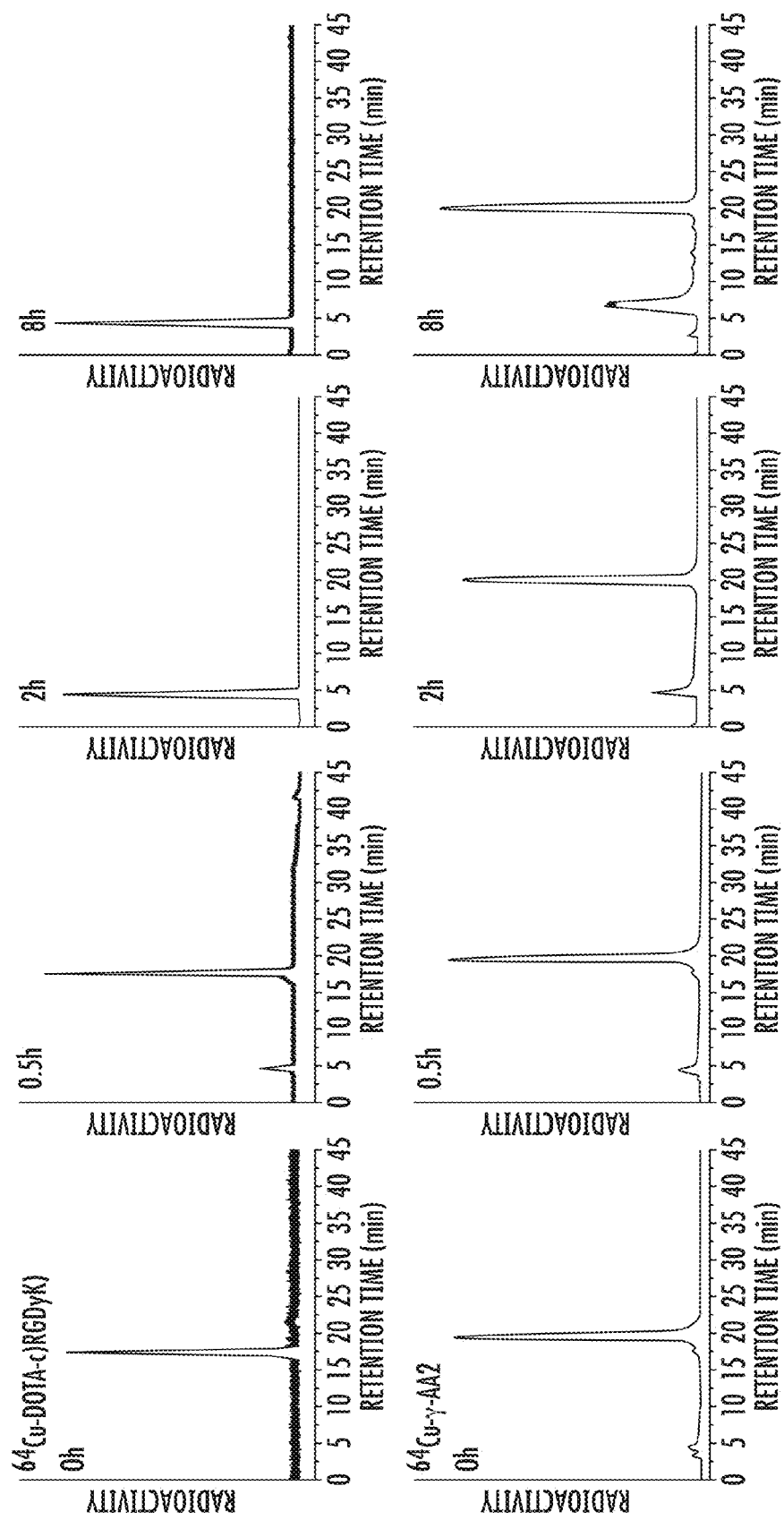
FIG. 4 is a series of graphs illustrating serial radio-HPLC profiles of $^{64}$Cu-DOTA-c(RGDyK) and [64]Cu-γ-AA2 before and after incubation in pronase at 37° C.

$^{64}$Cu-γ-AA2 exhibited markedly better stability than $^{64}$Cu-DOTA-c(RGDyK) (FIG. 4). The stability of c(RGDyK) is expected to be significantly higher than the natural RGD peptide, attributed to the inclusion of a D-Tyr residue and head-to-tail cyclization, both of which are proven strategies for improving the stability of natural peptides. However, ~8% of $^{64}$Cu-DOTA-c(RGDyK) was already degraded at 0.5 h post-treatment, with 100% enzyme degradation at 2 h and 8 h post-treatment. In comparison, $^{64}$Cu-γ-AA2 only had 4%, 8%, and 15% degradation at 0.5 h, 2 h, and 8 h post-treatment, respectively. The UV traces were similar to the radio-HPLC results (see FIG. 6). The fact that $^{64}$Cu-γ-AA2 is much more enzymatically stable than $^{64}$Cu-DOTA-c(RGDyK) makes γ-AApeptides a promising class of targeting ligands for PET imaging applications, which possess exceptional stability.

Figure 5A:
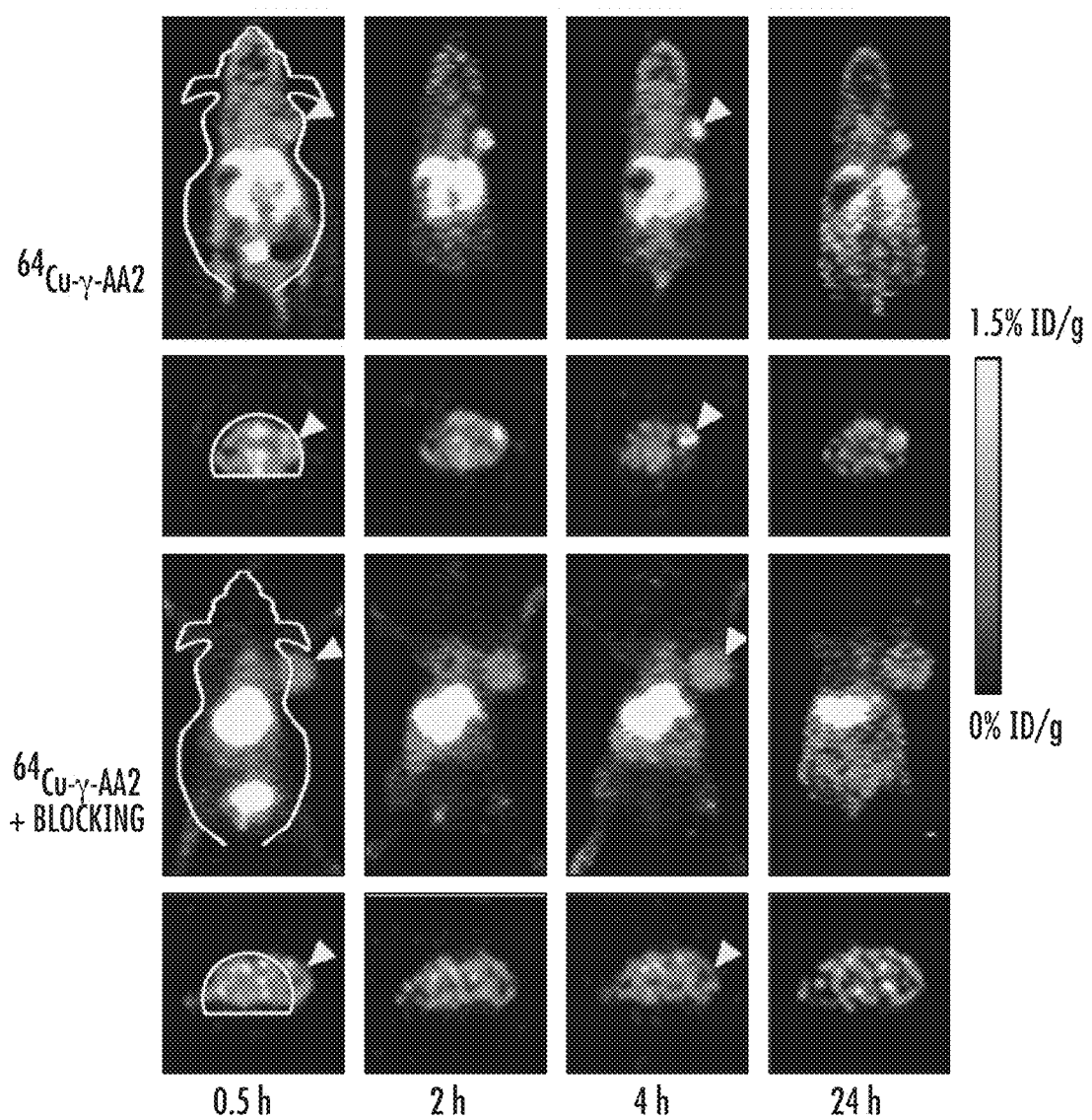
FIGS. 5A-5E illustrate serial PET imaging and biodistribution studies of [64]Cu-γ-AA2 in U87MG tumor-bearing mice.
Figure 5B:
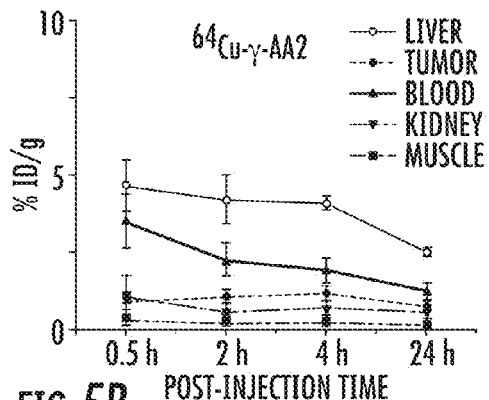
Figure 5C:
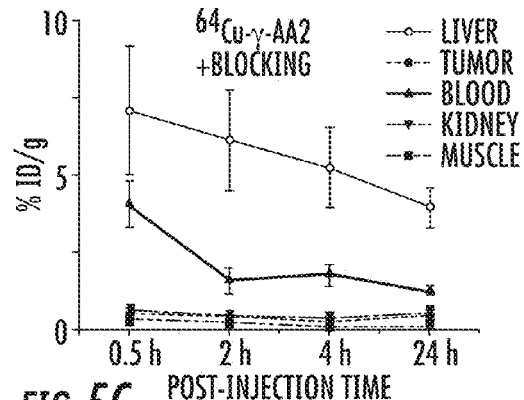
Figure 5D:
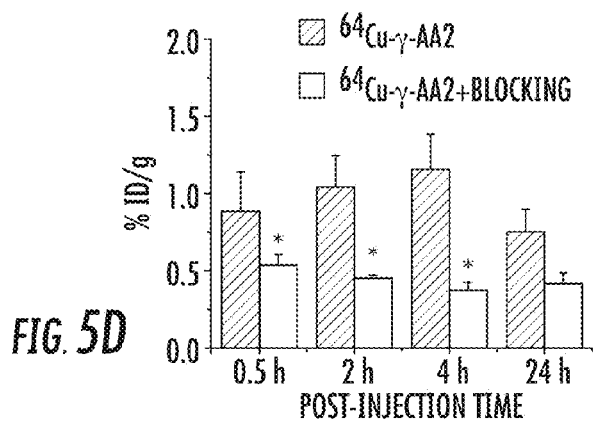

After demonstrating the excellent stability of $^{64}$Cu-γ-AA2 in vitro, serial in vivo PET imaging was carried out in the U87MG tumor model (which expresses high level of integrin $\alpha_v\beta_3$ on tumor vasculature and tumor cells[11, 13]) after intravenous injection of the tracer. PET scans at various time points post-injection (p.i.), as well as quantitative region-of-interest (ROI) analysis of the PET data, were performed as described previously.[14] Coronal and transaxial PET slices that contain the U87MG tumors are shown in FIG. 5A, and the quantitative data are shown in FIGS. 5B and 5C.

Uptake of $^{64}$Cu-γ-AA2 in the U87MG tumor was clearly visible as early as 0.5 h p.i., which remained persistent over time (0.9±0.3, 1.0±0.2, 1.1±0.2, and 0.7±0.2% ID/g at 0.5, 2, 4, and 24 h p.i. respectively; n=3; FIG. 5B). Excellent tumor contrast was observed, with tumor/muscle ratio of 3.8±0.9, 4.8±1.8, 5.8±1.4, and 8.3±3.9 at 0.5 h, 2 h, 4 h, and 24 h p.i. respectively (n=3). Since $^{64}$Cu-γ-AA2 undergoes both hepatobiliary and renal clearance, tracer uptake was also observed in the liver/kidneys.

Administering a blocking dose of the c(RGDyK) peptide reduced the U87MG tumor uptake significantly to 0.5±0.1, 0.4±0.1, 0.4±0.1, and 0.4±0.1% ID/g at 0.5, 2, 4, and 24 h p.i., respectively (n=3; P<0.05 at 0.5, 2, and 4 h p.i. when compared with mice injected with $^{64}$Cu-γ-AA2 only; FIGS. 5A-D), which demonstrated integrin $\alpha_v\beta_3$ specificity of the tracer in vivo. Liver uptake of $^{64}$Cu-γ-AA2 was higher in the blocking group, being 7.2±2.0, 6.1±1.6, 5.3±1.3, and 4.0±0.6% ID/g at 0.5, 2, 4, and 24 h p.i. respectively (n=3). Radioactivity in the blood (0.5±0.1, 0.4±0.1, 0.4±0.1, and 0.4±0.1% ID/g at 0.5, 2, 4, and 24 h p.i., respectively; n=3) was lower for the "blocking" group at early time points, indicating faster blood clearance of the tracer (FIGS. 5B-5C). After the last PET scans at 24 h p.i., all mice were euthanized for biodistribution studies to validate the in vivo PET data.

Figure 5E:
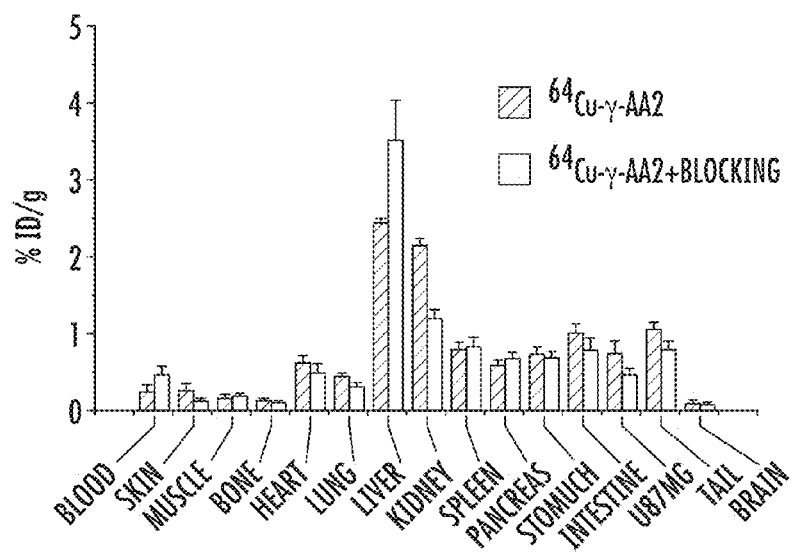

The % ID/g values of $^{64}$Cu-γ-AA2 in the tumor and various normal tissues obtained from ex vivo biodistribution studies (FIG. 5E) matched well with the results from ROI analysis of the PET scans, confirming that non-invasive imaging can enable accurate quantification of $^{64}$Cu-γ-AA2 distribution in vivo.

In summary, the $^{64}$Cu-labeled γ-AApeptide-based RGD mimetic exhibited comparable integrin $α_vβ_3$ binding affinity as the c(RGDyK) peptide but significantly higher resistance to enzymatic degradation and better in vivo stability, despite its shorter sequence and linear nature. Integrin $α_vβ_3$ specificity, fast blood clearance, and good tumor contrast of $^{64}$Cu-γ-AA2 established γ-AApeptides as a novel class of enzymatically stable targeting ligands for molecular imaging applications.

Materials, Synthesis, and Methods:

1. General Experimental Methods.

Fmoc protected α-amino acids and Knorr resin were obtained from Chem-Impex International, Inc. DOTA-NHS ester was purchased from Macrocyclics, Inc. (Dallas, Tex.). Pronase and Chelex 100 resin (50-100 mesh) were from Sigma-Aldrich (St. Louis, Mo.). Water and all buffers were of Millipore grade and pre-treated with Chelex 100 resin to ensure that the aqueous solution was heavy metal-free. All other reaction buffers and chemicals were from Thermo Fisher Scientific (Fair Lawn, N.J.). NMR spectra of γ-AApeptide building blocks were obtained on a Varian Inova 400. γ-AApeptide sequences were prepared on a Knorr resin in peptide synthesis vessels on a Burrell Wrist-Action shaker. The γ-AApeptides were analyzed and purified on a Waters HPLC with analytical and preparative modules, and the desired fractions were then lyophilized using a Labconco lyophilizer. Molecular weight of γ-AApeptides were identified on a Bruker AutoFlex MALDI-TOF mass spectrometer.

2. Synthesis of γ-AApeptide Building Blocks and Sequences.[8-10]

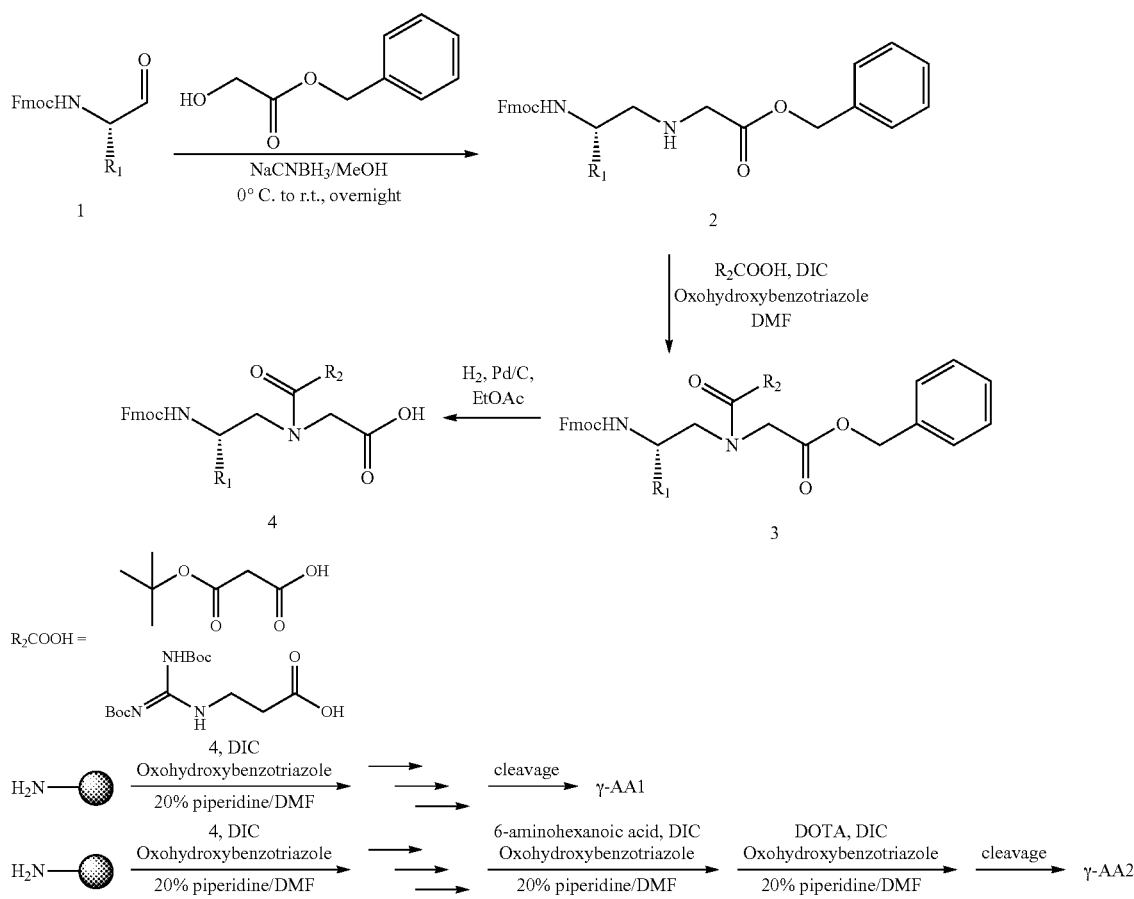

General Procedure

Synthesis of 2.[8-10]

To a glycine benzyl ester hydrochloride in 15 ml methanol in a 100 ml round bottom flask was added 1.1 equiv. of triethylamine and the reaction mixture was stirred at 0° C. for 15 min. Stoichiometric amount of a Fmoc protected amino acid aldehyde was added and the mixture was stirred for another 30 min. Catalytic amount of acetic acid was then added, followed by 2 equivalence of NaBH$_3$CN. The solution was stirred at 0° C. for 1 h and continued at room temperature overnight. The solvent was evaporated and 100 ml ethyl acetate and 100 ml saturated sodium bicarbonate solution were added to the residue. The organic layer was separated and washed with 100 ml brine, dried over anhydrous sodium sulfate, and removed in vacuo. Flash chromatography using ethyl acetate/hexane 1:1 gave 2 ($R_f$=0.2) as a colorless oil.

Synthesis of 3.

Compound 2, 1.2 equiv. of DIC, Oxohydroxybenzotriazole, and R$_2$COOH were stirred in 20 ml DMF overnight. The solution was then partitioned in 100 ml ethyl acetate and 100 ml water. The organic layer was separated and washed with water (3×100 ml) and Brine (2×100 ml), dried over anhydrous sodium sulfate, and then concentrated in vacuo. Flash chromatography using ethyl acetate/hexane 1:3 gave 3 ($R_f$=0.1) as a colorless oil.

Synthesis of 4.

3 in 20 ml of ethyl acetate was added to 10% Pd/C and hydrogenated at atmospheric pressure and room temperature overnight. The solution was evaporated and the residue was purified by flash chromatography 5-7% MeOH/$CH_2Cl_2$ to give 4 ($R_f$=0.2 in 7% MeOH/$CH_2Cl_2$) as a white foam solid.

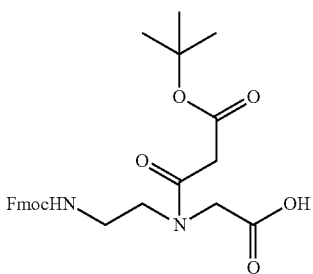

4a.

81% overall yield from 2. $^1$H NMR (600 MHz, DMSO-$d_6$) δ 7.89 (d, J=6.0 Hz, 2H), 7.68 (d, J=6.0 Hz, 2H), 7.66 (d, J=6.0 Hz, 2H), 7.43-7.38 (m, 2H), 7.35-7.31 (m, 2H), 4.32 (d, J=12 Hz, 1H), 4.28-4.19 (m, 2H), 3.97-3.93 (m, 2H), 3.40-3.26 (m, 4H), 3.19-3.09 (m, 2H), 1.38 (s, 9H), $^{13}$C NMR (150 MHz, DMSO-$d_6$) δ 171.9, 171.2, 167.6, 167.1, 167.0 166.98, 156.7, 156.6, 144.3, 144.2, 141.2, 141.1, 128.0, 127.5, 125.6, 125.5, 120.54, 120.51, 81.0, 80.9, 65.9, 48.4, 47.9, 47.1, 46.9, 42.4, 41.8, 39.1, 38.4, 28.1, 28.04. HRMS: [M+Na]$^+$ cacl: 505.1945. found: 505.1955.

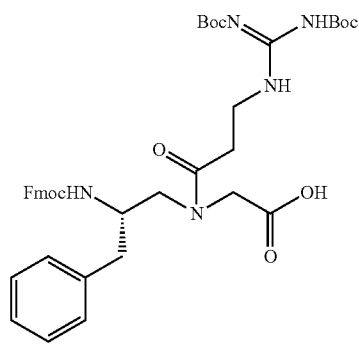

4b.

62% overall yield from 2. $^1$H NMR (600 MHz, DMSO-$d_6$) δ 11.4-10.8 (s, 1H), 8.87-8.76 (m, 1H), 7.88-7.86 (m, 2H), 7.60-7.55 (m, 2H), 7.41-7.14 (m, 10H), 4.21-4.16 (m, 2H), 4.15-4.10 (m, 2H), 4.09-4.06 (m, 1H), 4.03-4.01 (m, 1H), 3.71-3.31 (m, 4H), 3.06-2.46 (m, 4H). 1.42 (s, 9H), 1.39 (s, 9H). $^{13}$C NMR (150 MHz, DMSO-$d_6$) δ 172.3, 171.8, 171.5, 171.0, 156.2, 156.1, 154.93, 154.91, 152.0, 151.96, 144.2, 144.17, 144.1, 141.06, 139.2, 138.99, 129.5, 128.53, 128.5, 128.0, 127.4, 126.5, 126.3, 125.5, 125.4, 120.5, 84.0, 83.6, 65.8, 65.6, 52.4, 51.9, 51.4, 50.9, 50.3, 48.0, 47.1, 47.0, 38.1, 37.9, 37.5, 32.4, 32.2, 32.0, 31.7, 28.3, 27.9 HRMS: [M+Na]$^+$ cacl: 766.3422. found: 766.3426.

3. Solid Phase Synthesis, Purification, and Characterization of γ-AApeptides.

γ-AA1 and γ-AA2 were prepared on a Knorr resin in peptide synthesis vessels on a Burrell Wrist-Action shaker following the standard Fmoc chemistry of solid phase peptide synthesis protocol. Each coupling cycle included an Fmoc deprotection using 20% Piperidine in DMF, and 4 h coupling of 1.5 equiv of γ-AApeptide building blocks onto resin in the presence 2 equiv of DIC (diisopropylcarbodiimide)/Oxohydroxybenzotriazole in DMF. After the desired sequences were assembled, they were transferred into a 4 ml vial and cleaved from solid support in 48:50:2 TFA/$CH_2Cl_2$/triisopropylsilane overnight. Then solvent was evaporated and the residue was analyzed and purified on an analytical (1 ml/min) and a preparative Waters (20 ml/min) HPLC systems, respectively. The same methods were used by running 5% to 100% linear gradient of solvent B (0.1% TFA in acetonitrile) in A (0.1% TFA in water) over 40 min, followed by 100% solvent B over 10 min. The desired fractions were collected with >95% purity and lyophilized. The molecular weights of γ-AA1 and γ-AA2 were obtained on Bruker AutoFlex MALDI-TOF mass spectrometer using α-cyano-4-hydroxycinnamic acid as the matrix.

TABLE S1

MALDI-TOF MS analysis of γ-AApeptides.

| Sequence | Formula | Mass calcd. | Mass found |
|---|---|---|---|
| γ-AA1 | $C_{22}H_{34}N_8O_6$ | 506.6 | 507.2 (M + H$^+$) |
| γ-AA2 | $C_{44}H_{71}N_{13}O_{14}$ | 1006.0 | 1038.8 (M + 2NH$_4^+$ − 4H$^+$) |

4. Cell Lines and Animal Model.

U87MG human glioblastoma cell line was purchased from the American Type Culture Collection (ATCC, Manassas, Va.) and cultured in DMEM medium (Invitrogen, Carlsbad, Calif.) with 10% fetal bovine serum and incubated at 37° C. with 5% $CO_2$. Cells were used for in vitro and in vivo experiments when they reached ~75% confluence. All animal studies were conducted under a protocol approved by the University of Wisconsin Institutional Animal Care and Use Committee. To generate the xenograft tumor model, four- to five-week-old female nude mice were purchased from Harlan (Indianapolis, Ind.) and tumors were established by subcutaneously injecting 5×10$^6$ U87MG cells, suspended in 100 μL of 1:1 mixture of DMEM and Matrigel (BD Biosciences, Franklin lakes, N.J.), into the front flank of mice. Tumor sizes were monitored every other day and mice were used for in vivo experiments when the diameter of tumors reached 5-8 mm (typically 4 weeks after inoculation).

5. $^{64}$Cu-Labeling.

$^{64}$CuCl$_2$ (111 MBq) was diluted in 300 μL of 0.1 M sodium acetate buffer (pH 6.5) and added to 6 μg of γ-AA2. The reaction mixture was incubated for 30 min at 40° C. with constant shaking. $^{64}$Cu-γ-AA2 was purified by a Dionex Ultimate 3000 HPLC system equipped with a radioactivity and UV detector using a C-18 column. A solvent gradient (A: water with 0.1% TFA; B: acetonitrile with 0.1% TFA) was used, where solvent B was gradually increased from 5% to 65% over a period of 30 min. After collection of the radioactive peak, acetonitrile was removed from the solution with continuous argon flow. The remaining solution was reconstituted into a final concentration of 1×PBS. The tracer was passed through a 0.2 μm syringe filter before in vivo experiments.

6. Flow Cytometry Studies.

The binding affinity and specificity of FITC-γ-AA1 for integrin $\alpha_v\beta_3$ was evaluated in U87MG cells in a binding buffer (20 mM Tris, 150 mM NaCl, 2 mM $CaCl_2$, 1 mM $MgCl_2$, 1 mM $MnCl_2$, 0.10% BSA pH=7.4) at 37° C., by fluorescence-activated cell sorting (FACS) analysis. Briefly, cells were harvested and suspended in the binding buffer at a concentration of 5×10⁶ cells/mL. The cells were incubated with FITC-c(RGDyK) or FITC-γ-AA1 (5 µg/mL) for 30 min at RT, washed three times with cold PBS, and centrifuged at 1,000 rpm for 5 min. Two µM of c(RGDyK) was used for "blocking" studies of the two FITC-labeled agents. Afterwards, the cells were washed and analyzed by FACS using a BD FACSCalibur 4-color analysis cytometer, which is equipped with 488 nm and 633 nm lasers (Becton-Dickinson, San Jose, Calif.) and FlowJo analysis software (Tree Star, Inc., Ashland, Oreg.).

7. Enzymatic Stability of $^{64}$Cu-γ-AA2 and $^{64}$Cu-DOTA-c(RGDyK).

Figure 6:
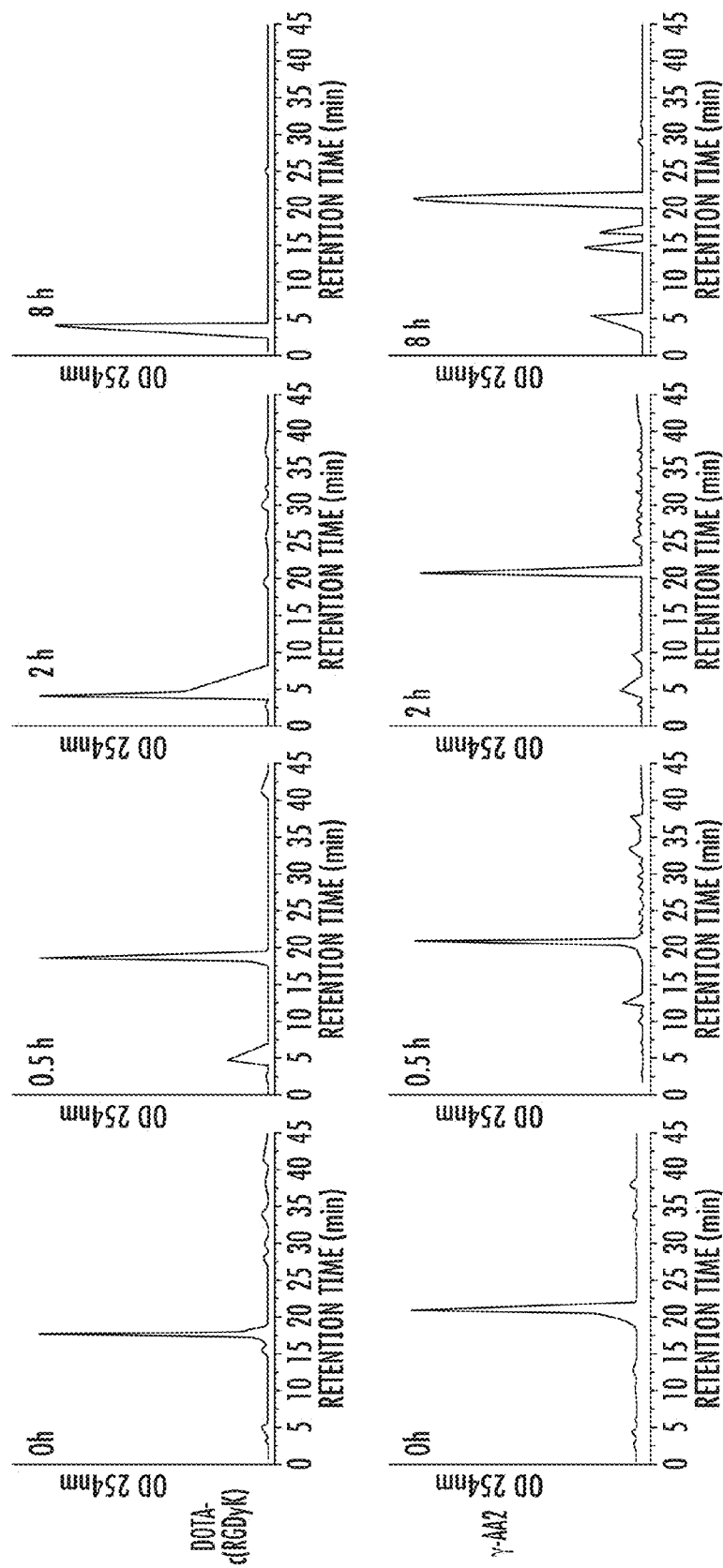
FIG. 6 is a series of graphs illustrating serial UV-HPLC profiles of $^{64}$Cu-DOTA-c(RGDyK) and [64]Cu-γ-AA2 before and after incubation in pronase at 37° C.

Approximately 148 MBq of $^{64}$Cu-γ-AA2 or $^{64}$Cu-DOTA-c(RGDyK) was incubated with 0.1 mg/ml pronase at 37° C. in 100 mM of ammonium bicarbonate buffer (pH 7.8) for 24 h, respectively. One fourth of the reaction mixtures were analyzed by radio-HPLC at 0.5 h, 2 h, and 8 h post-treatment and compared to evaluate the stability of the two tracers. The Radio-HPLC traces are shown FIG. 4, and the UV HPLC traces are shown in FIG. 6. Both confirmed the marked enhanced enzymatic stability of $^{64}$Cu-γ-AA2 over $^{64}$Cu-DOTA-c(RGDyK).

8. PET Imaging and Biodistribution Studies.

PET scans were performed using an Inveon microPET/microCT rodent model scanner (Siemens Medical Solutions USA, Inc.). Each U87MG tumor-bearing mouse was injected with 5-10 MBq of the PET tracer via tail vein and 5 minute static PET scans were performed at various time points post-injection (p.i.). The images were reconstructed using a maximum a posteriori (MAP) algorithm, with no attenuation or scatter correction. For each microPET scan, three-dimensional (3D) regions-of-interest (ROIs) were drawn over the tumor and major organs by using vendor software (Inveon Research Workplace [IRW]) on decay-corrected whole-body images. Assuming a tissue density of 1 g/mL, the ROIs were converted to MBq/g using a conversion factor (pre-determined using a 20 mL centrifuge tube filled with ~37 MBq of $^{64}CuCl_2$ as a phantom), and then divided by the total administered radioactivity to obtain an image ROI-derived percentage injected dose per gram of tissue (% ID/g). Another group of three U87MG tumor-bearing mice was each injected with the similar amount of $^{64}$Cu-γ-AA2 along with 10 mg/kg dose of c(RGDyK) to evaluate the integrin $\alpha_v\beta_3$ specificity of $^{64}$Cu-γ-AA2 in vivo (i.e., blocking experiment).

Biodistribution studies were carried out to confirm that the quantitative tracer uptake values based on PET imaging truly represented the radioactivity distribution in tumor-bearing mice. After the last PET scans at 24 h p.i., mice were euthanized and blood, U87MG tumor, and major organs/tissues were collected and wet-weighed. The radioactivity in the tissue was measured using a gamma-counter (Perkin Elmer) and presented as % ID/g (mean±SD).

Statistical Analysis

Quantitative data were expressed as mean±SD. Means were compared using Student's t-test. P values <0.05 were considered statistically significant.

Example 1 References, Each of which is Incorporated by Reference Herein

1. S. S. Gambhir, J. Czernin, J. Schwimmer, D. H. Silverman, R. E. Coleman and M. E. Phelps, *J Nucl Med*, 2001, 42, 1S-93S.
2. R. Weissleder and M. J. Pittet, *Nature*, 2008, 452, 580-589.
3. W. Cai and X. Chen, *J Nucl Med*, 2008, 49 Suppl 2, 113S-128S.
4. J. Folkman, *N Engl J Med*, 1971, 285, 1182-1186.
5. (a) W. Cai, G. Niu and X. Chen, *Curr Pharm Des*, 2008, 14, 2943-2973; (b) R. Haubner, W. A. Weber, A. J. Beer, E. Vabuliene, D. Reim, M. Sarbia, K. F. Becker, M. Goebel, R. Hein, H. J. Wester, H. Kessler and M. Schwaiger, *PLoS Med.*, 2005, 2, e70; (c) E. S. Mittra, M. L. Goris, A. H. Iagaru, A. Kardan, L. Burton, R. Berganos, E. Chang, S. Liu, B. Shen, F. T. Chin, X. Chen and S. S. Gambhir, *Radiology*, 2011, 260, 182-191.
6. W. Cai and X. Chen, *Anti-Cancer Agents Med Chem*, 2006, 6, 407-428.
7. G. Hao, A. Hajibeigi, L. M. De León-Rodríguez, O. K. Öz and X. Sun, *Am J Nucl Med Mol Imaging*, 2011, 1, 65-75.
8. Y. Niu, Y. Hu, X. Li, J. Chen and J. Cai, *New J Chem*, 2011, 35, 542-545.
9. Y. Niu, A. J. Jones, H. Wu, G. Varani and J. Cai, *Org Biomol Chem*, 2011, 9, 6604-6609.
10. Y. Niu, S. Padhee, H. Wu, G. Bai, L. Harrington, W. N. Burda, L. N. Shaw, C. Cao and J. Cai, *Chem Commun*, 2011, 47, 12197-12199.
11. W. Cai, Y. Wu, K. Chen, Q. Cao, D. A. Tice and X. Chen, *Cancer Res*, 2006, 66, 9673-9681.
12. Y. Hu, X. Li, S. M. Sebti, J. Chen and J. Cai, *Bioorg Med Chem Lett*, 2011, 21, 1469-1471.
13. W. Cai, D. W. Shin, K. Chen, O. Gheysens, Q. Cao, S. X. Wang, S. S. Gambhir and X. Chen, *Nano Lett*, 2006, 6, 669-676.
14. Y. Zhang, H. Hong, J. W. Engle, Y. Yang, T. E. Barnhart, and W. Cai, *Am J Nucl Med Mol Imaging*, 2012, 2, 1-13.

Example 2

Design and Synthesis of Monomeric Linear γ-AApeptides for RGD Mimicry

Figure 7:
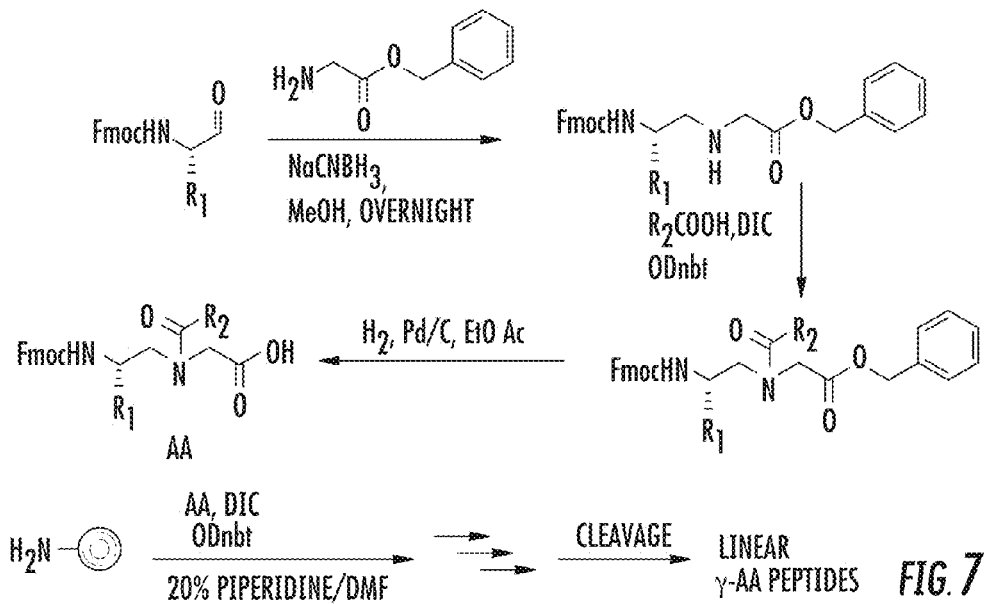
FIG. 7 illustrates an embodiment of a method of synthesis of embodiments of linear γ-AApeptides of the present disclosure that mimic RGD peptides.

Design of γ-AApeptides:

Synthesis of γ-AApeptides containing a RGD-mimicking fragment adjacent to a functional group R1, with the linear structures of Formula 1 was described above. A few hydrophobic R1 groups have been made as shown in γ-AA1-γ-AA7 above. The present example explores the effect of other hydrophobic groups, polar groups, and charged groups, which directly come from the derivatization of amino acids (FIG. 7). Additionally, the lengths of side chains of the RGD-mimicking fragment will be varied (R2 and R3), since only N,N'-Di-(Boc)-guanidino propionic acid and mono-t-butyl malonate were used to introduce guanidino and carboxyl groups (Boc and t-butyl protecting groups were removed during TFA cleavage from the solid phase).[76-78] Thus, the side chains with one more or less carbon (acylation using N,N'-Di-(Boc)-guanidino acetic acid, N,N'-Di-(Boc)-guanidino butyric acid and mono-t-butyl succinate) are studied. Although RGE (Arg-Gly-Glu) containing peptides do not bind to integrins,[93-95] the effect of length in γ-AApeptides for RGD mimicry are to be explored, since γ-AApeptides and α-peptides have different backbones and spatial confirmations.[76]

Synthesis of γ-AApeptides.

The synthesis of γ-AApeptides is carried out on Rink-amide resin following standard Fmoc chemistry protocol.[76-78] Briefly, γ-AApeptide building blocks are synthesized by the synthetic route shown in FIG. 7. The γ-AApeptides are then prepared by assembling the desired building blocks together and cleaving them from the solid support.

Design and Synthesis of Multimeric Linear γ-AApeptides for RGD Mimicry

Figure 8:
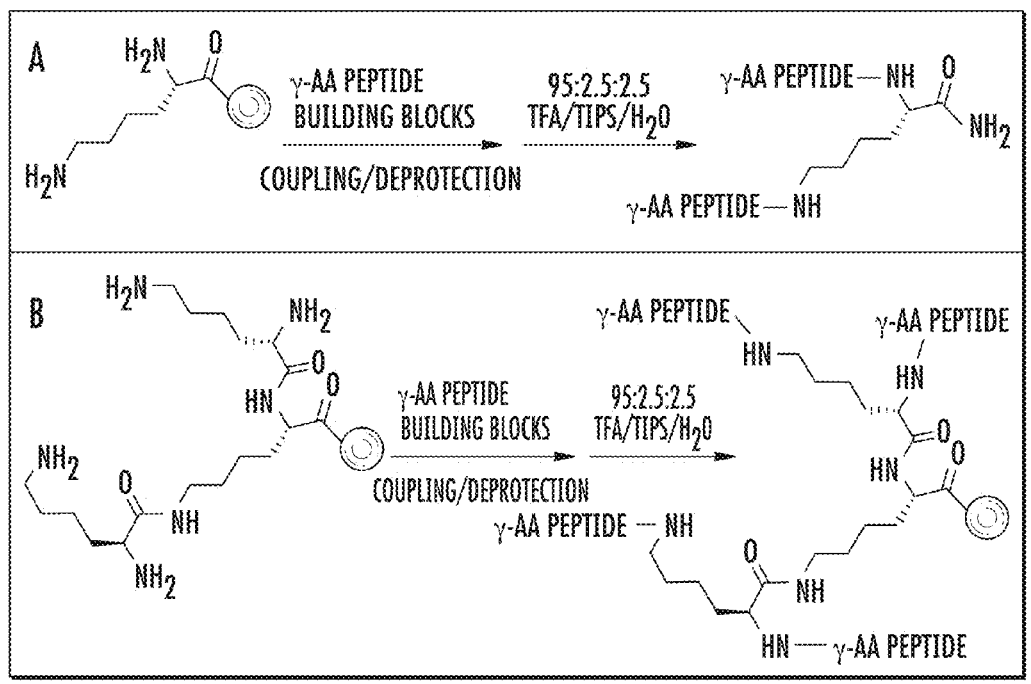
FIG. 8 illustrates an embodiment of a method of synthesizing tetrameric γ-AApeptide-based RGD mimetics.

Since interactions between integrins and ECM proteins may involve multiple binding sites, the introduction of multiple RGD binding elements in a molecule may increase the binding specificity and affinity.[92] Indeed, both these preliminary studies and previous reports support this.[50] However, it is also noted that the activity of multimeric RGD peptides does not continuously increase as the number of RGD peptide goes up, possibly due to the increased steric hindrance, which may impair the binding affinity.[50] As such, the present example explores the synthesis and structure-function relationship of dimeric and tetrameric linear γ-AApeptides for integrin recognition. The monomeric γ-AApeptides having comparable or better binding affinity than c(RGDyK) are initially used for dimer and tetramer preparation. The synthesis is straightforward (FIG. 8) on solid phase and has been achieved in our group. Basically, dimeric RGD mimetics are prepared by growing the desired γ-AApeptides on the α-amino group and the amino group from the side chain of a lysine on solid support (FIG. 8a), while tetrameric RGD mimetics are generated by elongating the desired γ-AApeptides on the four amino groups from two lysine residues, which have been conjugated to another lysine residue on the solid phase (FIG. 8b).

Cyclic γ-AApeptides that Mimic the Structural and Functional Motif of RGD.

Building upon the preliminary results, a focused library of cyclic γ-AApeptides that can mimic the RGD-binding motif will be designed and synthesized. Such cyclic γ-AApeptides will be tested for their binding specificity and affinity towards integrin $\alpha_v\beta_3$.

Based on preliminary data, cyclization of γ-AApeptides can further improve their binding specificity and affinity towards integrin $\alpha_v\beta_3$, and to enhance their stability against proteolytic degradation.[10, 92, 98] Both cyclic γ-AApeptide based penta- and hexa-RGD mimetics will be prepared and tested for their binding affinity towards the integrin $\alpha_v\beta_3$.

Figure 9:
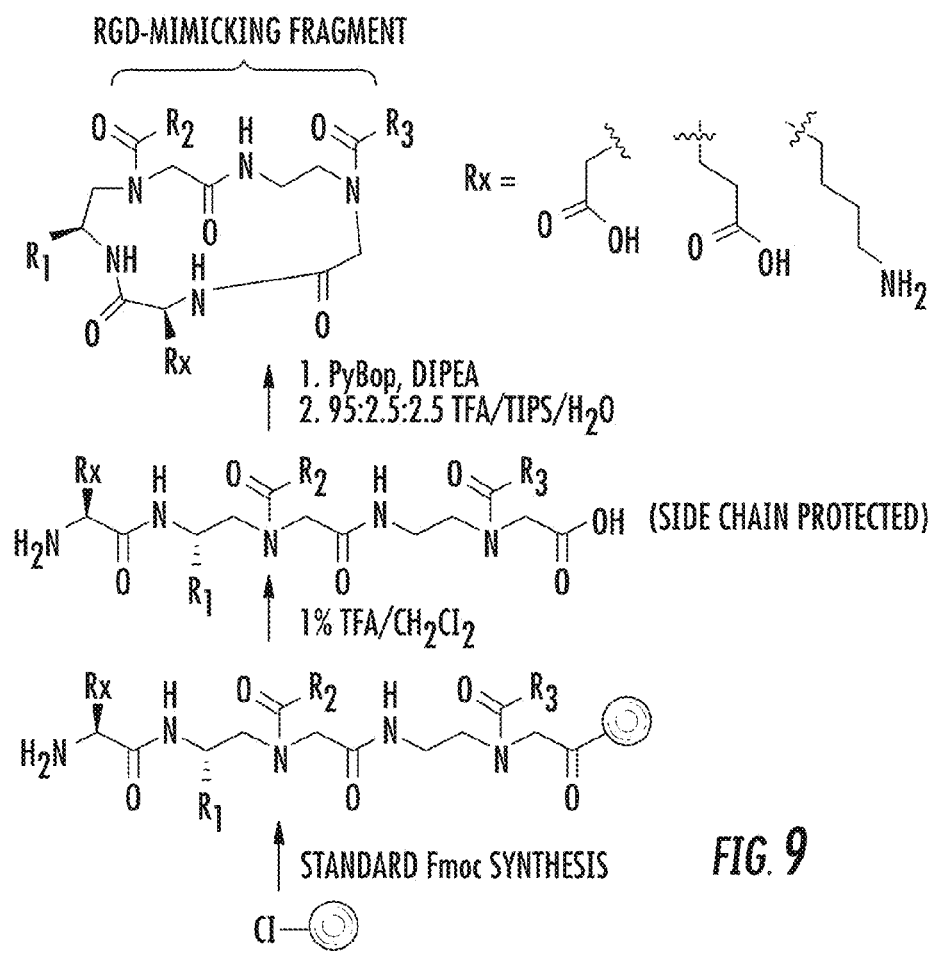
FIG. 9 illustrates an embodiment of a method of synthesis of cyclic γ-AApeptides that mimic cyclic penta-RGD peptide. Representative embodiments for Rx are shown. R1, R2 and R3 can be as described in Formula I, below.

Design and Synthesis of Monomeric Cyclic γ-AApeptides Mimicking Cyclic RGD Pentapeptides Design:

Since one γ-AApeptide building block is comparable to two amino acid residues in terms of length, an amino acid residue is introduced in addition to the linear sequences shown in Formula I, which are comparable to tetrapeptides. The general structure of such cyclic γ-AApeptides is shown in FIG. 9. R1, R2 and R3 groups will be explored using the approach described above. As to the Rx groups, since they do not participate in RGD recognition, and they are also not adjacent to the RGD-mimicking fragment in γ-AApeptides, they are expected to have minimal effect on the binding affinity towards integrin $\alpha_v\beta_3$. As such, as the initial attempt, Lys, Glu, Asp are introduced in addition to two γ-AApeptide building blocks. These amino acid residues contain either amino or carboxyl groups that can be used for conjugation with other moieties in the future, e.g., preparation of dimers or tetramers, and radio-labeling for targeted imaging, etc.

Synthesis:

The synthesis of cyclic γ-AApeptide penta-RGD mimetics is accomplished on solid phase using highly acid-labile 2-chlorotrityl resin (FIG. 9). Briefly, the desired sequences are assembled on the solid support, and then cleaved in 1% TFA/CH$_2$Cl$_2$, at which condition the protecting groups on the side chains of sequences are not affected. The cleaved sequences then undergo cyclization using PyBop/DIPEA as the activation agent, and the final deprotection in 95:2.5:2.5 TFA/TIPS/H$_2$O provides the desired cyclic γ-AApeptides penta-RGD mimetics.

Figure 10:
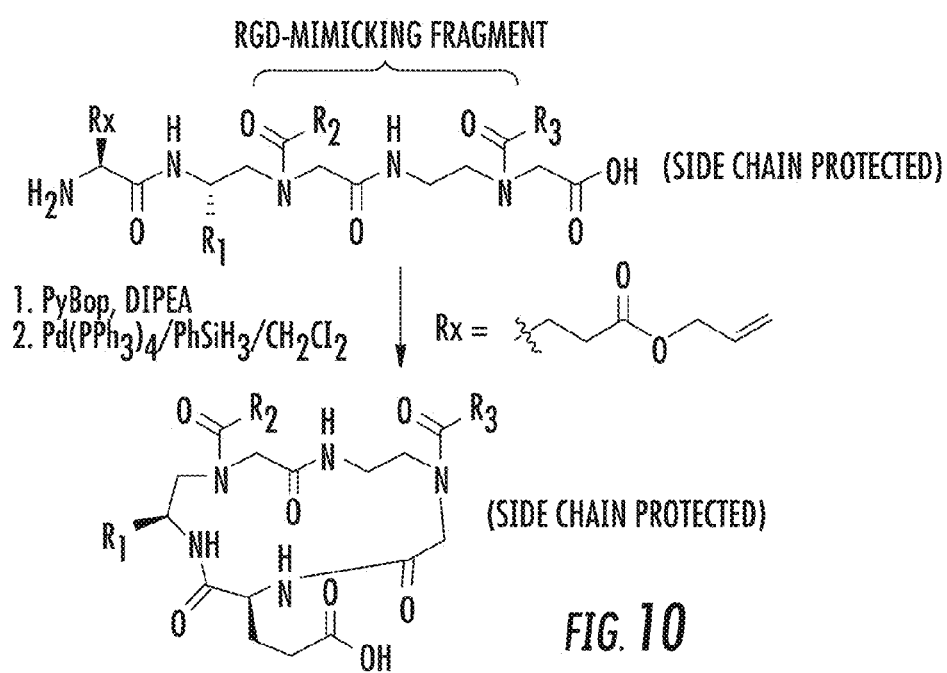
FIG. 10 illustrates an embodiment for the synthesis of protected cyclic γ-AApeptide fragments for the preparation of multimeric cyclic γ-AApeptide-based penta-RGD mimetics of the present disclosure.

Design and Synthesis of Multimeric Cyclic γ-AApeptides Mimicking Cyclic Penta-RGD Peptides As mentioned above, dimeric and tetrameric cyclic γ-AApeptides mimicking cyclic penta-RGD peptides will be synthesized for those monomers having an affinity comparable to or better than that of c(RGDyK). To facilitate the synthesis, the amino acid used in the protected cyclic γ-AApeptides is the allyl protected Glu (FIG. 10). After cleavage and cyclization, allyl protecting group(s) are specifically removed using catalyst Pd(PPh$_3$)$_4$. The protected cyclic γ-AApeptide fragments are then used to conjugate to solid phase to prepare both dimers and tetramers as shown in FIG. 8.

Figure 11:
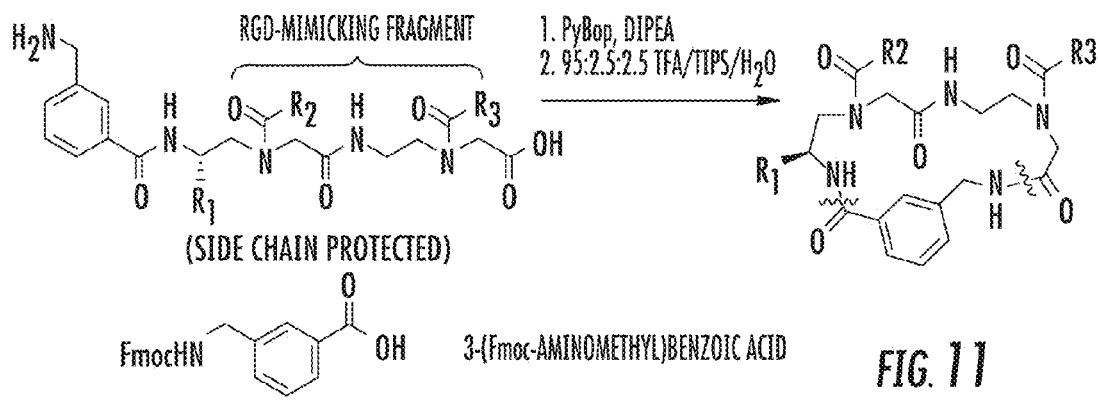
FIG. 11 illustrates an embodiment for the synthesis of protected cyclic γ-AApeptides of the present disclosure that mimic cyclic penta-RGD peptide.

Design and Synthesis of Monomeric Cyclic γ-AApeptides Mimicking Cyclic RGD Hexapeptides Cyclic γ-AApeptides containing a rigid aromatic ring (FIG. 11) will also be designed and synthesized for the enhancement of the selectivity on integrin recognition.[92] Such cyclic γ-AApeptides are cyclic hexapeptide mimetics since the aromatic ring-containing unnatural amino acid is comparable to two amino acid residues in length. Also, introduction of more diverse functional groups other than the rigid aromatic ring (e.g., another γ-AApeptide building block, as seen in γ-AA6) into cyclic γ-AApeptides will be further explored. The synthesis is carried out on a 2-chlorotrityl resin as described in FIG. 9, and the aromatic ring is introduced using commercially available 3-(Fmoc-aminomethyl) benzoic acid (FIG. 11).

Figure 12:
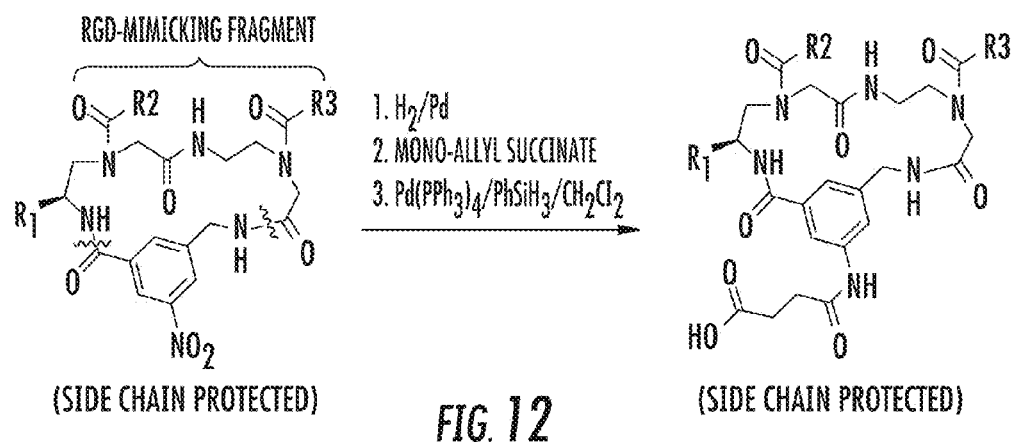
FIG. 12 illustrates an embodiment for the synthesis of protected cyclic γ-AApeptide fragments for the preparation of multimeric cyclic γ-AApeptide based hex-RGD mimetics of the present disclosure.

Design and Synthesis of Multimeric Cyclic γ-AApeptides Mimicking Cyclic RGD Hexapeptides The dimeric and tetrameric cyclic γ-AApeptides mimicking cyclic hexa-RGD peptides is carried out for those monomers having the affinity comparable or better than that of c(RGDyK). In order to tether the cyclic γ-AApeptide mimetics to the solid phase for the preparation of dimers and tetramers, as shown in FIG. 8, 3-nitro-5-(Fmoc-aminomethyl)-benzoic acid[99] is introduced into the cyclic structures (FIG. 12). Such a linker contains a nitro group that can be reduced to the amino group through hydrogenation, which is conjugated to mono-allyl succinate, followed by the removal of the allyl protecting group to produce the side-chain protected cyclic fragments. The product can be readily tethered to solid phase for the preparation of dimeric and tetrameric peptidomimetics.

Anticipated Results and Alternative Strategies

Figure 13:
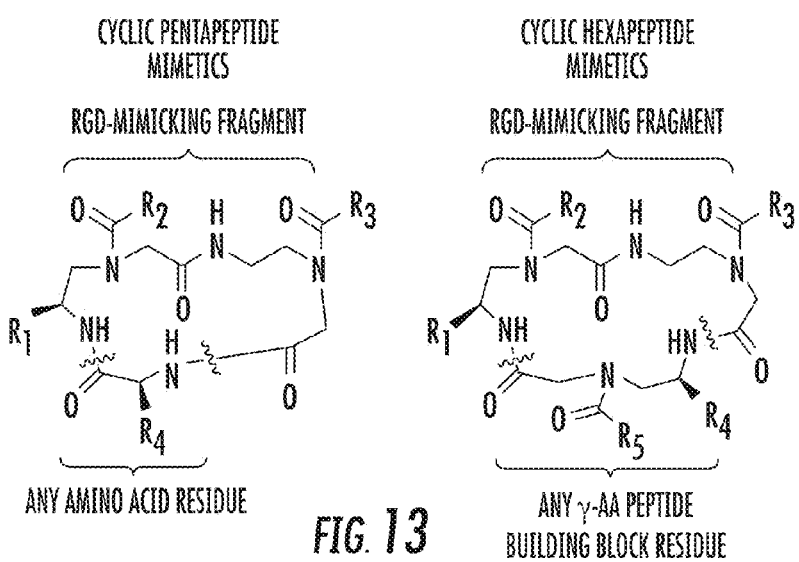
FIG. 13 illustrates the structures of cyclic γ-AApeptide mimicking penta- and hexa-RGD peptides of the present disclosure using either amino acids or γ-AApeptide building blocks as linkers.

The procedures above will generate a focused library of cyclic γ-AApeptides to mimic the RGD motif for the recognition of integrin $\alpha_v\beta_3$. The synthetic protocol has been highly formulated in the lab. The proposed linkers will initially be focused on a few commonly used ones in cyclic RGD peptides. Although it is expected that potent $\alpha_v\beta_3$ binders of cyclic γ-AApeptides containing these linkers will be identified based on the preliminary studies, exploration of other linkers (FIG. 13) by including different amino acids (for pentapeptide mimicry) or γ-AApeptide building blocks (for hexapeptide) is of significance and will be further explored. Such efforts will lead to the further improvement of molecules that can specifically target $\alpha_v\beta_3$.

Identification of Potent γ-AApeptides that can Specifically Recognize Integrin $α_vβ_3$ Through Competitive Solid-Phase Integrin Binding Assay, Cell Adhesion Assay, and PET Imaging Using In Vivo Mouse Model.

We will investigate the binding affinity and specificity of γ-AApeptides obtained above towards integrin $α_vβ_3$ using both competitive solid-phase integrin binding assay and cell adhesion assay in vitro, similar to the process described in Example 1, above. The γ-AApeptides that have binding activity comparable or better than the positive control c(RGDyK) will be used for targeted PET imaging in mice bearing inoculated glioblastoma tumor.

The prepared γ-AApeptides will first be tested for their binding affinity towards integrin $α_vβ_3$ using competitive solid-phase integrin binding assay. c(RGDyK) ($α_vβ_3$ specific) will be used as the positive control. The ones that have binding affinity c(RGDyK) will be used in tumor cell (glioblastoma U87MG cell line, overexpressing $α_vβ_3$) adhesion assay to further evaluate their capability to bind to $α_vβ_3$ in a cellular environment. Then ones that have comparable or better activity than c(RGDyK) will be conjugated with DOTA, labeled with $^{64}Cu$, and tested in vivo for targeted PET imaging in mice bearing inoculated glioblastoma U87MG cells. Actually, cyclic RGD mimetic $^{64}Cu$-DOTA-γ-AA6 (see Example 1) and dimeric RGD mimetic $^{64}Cu$-DOTA-γ-AA7 are currently under investigation by PET imaging on the glioblastoma U87MG-bearing mouse model for the evaluation of their ability for targeted tumor imaging in vivo.

Competitive Solid-Phase Integrin Binding Assay[98, 110, 111]

This assay is used to determine the capability of γ-AApeptides to inhibit the interactions between integrin $α_vβ_3$ and vitronectin. Briefly, flat-bottom ELISA plates are coated overnight at RT with 100 μL/well of 0.4 μg/mL human $α_vβ_3$ (Millipore) in TS buffer (20 mM Tris-HCl pH 7.5, 150 mM NaCl, 1 mM $CaCl_2$, 1 mM $MgCl_2$, and 1 mM $MnCl_2$). The wells are blocked for 2 h with 150 μL/well of TSB buffer (TS buffer containing 1% BSA), and washed with 200 μL/well of PBST buffer (10 mM Na2HPO4 pH 7.5, 150 mM NaCl, and 0.01% Tween 20). Serial concentrations of γ-AApeptides and the controls are mixed with 1 μg/mL of human vitronectin (BD Biosciences), which has been biotinylated with sulfo-NHS-LC-LC-biotin (Fisher scientific), and 100 μL/well of these solutions are incubated for 2 h. The plate is then washed five times with PBST buffer, and 100 μL/well of 0.25 μg/mL neutravidin-horseradish peroxidase (HRP) conjugate (Thermo scientific) in TSB buffer is added to the plate and incubated for 1 h. After another 5-fold wash, the plate is developed by adding 100 μL/well of o-phenylenediamine hydrochloride (OPD, Sigma-Aldrich) solution (0.1% in 24 mM sodium citrate, 50 mM $Na_2HPO_4$, 0.012% $H_2O_2$, pH 5.0). After 15 min the reaction is quenched with 3 M $H_2SO_4$ and the absorbance at 492 nm is recorded. Percent (%) inhibition is calculated from an average of three separate determinations relative to buffer controls (no test compound added).

Cell Adhesion Assay[50, 106, 112]

Although competitive solid-phase integrin binding assay will give the binding activity of γ-AApeptides towards the integrin $α_vβ_3$, cell adhesion assays will also be carried out to further confirm their binding affinity and specificity in a cellular environment, so as to provide the foundation for their application in vivo in the future. Glioblastoma U87MG cancer cells (overexpress integrin $α_vβ_3$) are used for cell adhesion assay. Briefly, ninety-six-well plates are coated with 2 μg/mL of vitronectin in phosphate-buffered saline at 4° C. overnight and treated with 2% bovine serum albumin for 1 h at 37° C. U87MG cells ($2×10^5$ cells/mL) with various concentrations of γ-AApeptides and controls in 100 μL of serum-free Dulbecco's modified Eagle's medium containing 0.1% bovine serum albumin are incubated for 20 min at 37° C. The resulting mixture is added to the plates and incubated for 1 h at 37° C. Plates treated with only bovine serum albumin are used as a negative control. After removal of the medium by aspiration, 0.04% crystal violet solution is added and incubated for 10 min at room temperature. The wells are washed 3 times with phosphate-buffered saline, and 20 μL of Triton X-100 is added for permeabilization. Distilled water (80 μL) is then added, and the number of adherent cells is assessed with a microplate reader (measurement wavelength, 550 nm; reference wavelength, 630 nm).

PET Imaging on Mice of Tumor Model[50, 66, 89, 108]

All animal studies are conducted under a protocol approved by the University of Wisconsin Institutional Animal Care and Use Committee. Four- to five-week-old female athymic nude mice are purchased from Harlan (Indianapolis, Ind.) and tumors are established by subcutaneously injecting $5×10^6$ U87MG cells, suspended in 100 μL of 1:1 mixture of RPMI 1640 and matrigel (BD Biosciences, Franklin lakes, NJ), into the front flank of mice. The tumor sizes are monitored every other day and the animals are subjected to in vivo experiments when the size of the tumors reaches 500 $mm^3$.[113, 114]

PET scans are performed using an Inveon microPET/microCT rodent model scanner (Siemens Medical Solutions USA, Inc.). Each U87MG tumor-bearing mouse is injected with 5-10 MBq of the PET tracer ($^{64}Cu$-DOTA-γ-AApeptides) via tail vein and 5 minute static PET scans are performed at various time points post-injection (p.i.). The images are reconstructed using a maximum a posteriori (MAP) algorithm, with no attenuation or scatter correction. For each microPET scan, three-dimensional (3D) regions-of-interest (ROIs) are drawn over the tumor and major organs by using vendor software (Inveon Research Workplace [IRW]) on decay-corrected whole-body images. Assuming a tissue density of 1 g/mL, the ROIs are converted to MBq/g using a conversion factor (pre-determined using a 20 mL centrifuge tube filled with ~37 MBq of $^{64}CuCl_2$ as a phantom), and then divided by the total administered radioactivity to obtain an image ROI-derived percentage injected dose per gram of tissue (% ID/g). Another group of three U87MG tumor-bearing mice is each injected with the similar amount of $^{64}Cu$-DOTA-γ-AApeptides along with 10 mg/kg dose of c(RGDyK) to evaluate the integrin $α_vβ_3$ specificity of $^{64}Cu$-γ-AApeptides in vivo (i.e. blocking experiment). All the experiment described above use $^{64}Cu$-DOTA-c(RGDyK) as the positive control.

Biodistribution studies are carried out to confirm that the quantitative tracer uptake values based on PET imaging truly represented the radioactivity distribution in tumor-bearing mice. After the last PET scans at 24 h p.i., mice are euthanized and blood, U87MG tumor, and major organs/tissues are collected and wet-weighed. The radioactivity in the tissue is measured using a gamma-counter (Perkin Elmer) and presented as % ID/g (mean±SD).

Example 2 References, Each of which is Incorporated by Reference Herein

1. Okamoto, I.; Yoshioka, H.; Takeda, K.; Satouchi, M.; Yamamoto, N.; Seto, T.; Kasahara, K.; Miyazaki, M.; Kitamura, R.; Ohyama, A.; Hokoda, N.; Nakayama, H.; Yoshihara, E.; Nakagawa, K. Phase I Clinical Study of the Angiogenesis Inhibitor TSU-68 Combined with Carboplatin and Paclitaxel in Chemotherapy-Naive Patients with Advanced Non-small Cell Lung Cancer. *J Thorac Oncol* 2011, Advanced article.
2. Sridhar, S. S.; Shepherd, F. A. Targeting angiogenesis: a review of angiogenesis inhibitors in the treatment of lung cancer. *Lung Cancer* 2003, 42 Suppl 1, S81-91.
3. Shijubo, N.; Kojima, H.; Nagata, M.; Ohchi, T.; Suzuki, A.; Abe, S.; Sato, N. Tumor angiogenesis of non-small cell lung cancer. *Microsc Res Tech* 2003, 60, 186-98.
4. Shepherd, F. A.; Sridhar, S. S. Angiogenesis inhibitors under study for the treatment of lung cancer. *Lung Cancer* 2003, 41 Suppl 1, S63-72.
5. Bussolino, F.; Caccavari, F.; Valdembri, D.; Serini, G. Angiogenesis: a balancing act between integrin activation and inhibition? *Eur Cytokine Netw* 2009, 20, 191-6.
6. Kim, E. Y.; Bang, J. Y.; Chang, S. I.; Kang, I. C. A novel integrin alpha5beta1 antagonistic peptide, A5-1, screened by Protein Chip system as a potent angiogenesis inhibitor. *Biochem Biophys Res Commun* 2008, 377, 1288-93.
7. Mahabeleshwar, G. H.; Chen, J.; Feng, W.; Somanath, P. R.; Razorenova, O. V.; Byzova, T. V. Integrin affinity modulation in angiogenesis. *Cell Cycle* 2008, 7, 335-47.
8. Mahabeleshwar, G. H.; Feng, W.; Phillips, D. R.; Byzova, T. V. Integrin signaling is critical for pathological angiogenesis. *J Exp Med* 2006, 203, 2495-507.
9. Kerr, J. S.; Slee, A. M.; Mousa, S. A. The alpha v integrin antagonists as novel anticancer agents: an update. *Expert Opin Investig Drugs* 2002, 11, 1765-74.
10. Mas-Moruno, C.; Rechenmacher, F.; Kessler, H. Cilengitide: the first anti-angiogenic small molecule drug candidate design, synthesis and clinical evaluation. *Anticancer Agents Med Chem* 2010, 10, 753-68.
11. Liu, Z.; Wang, F.; Chen, X. Integrin targeted delivery of radiotherapeutics. *Theranostics* 2011, 1, 201-10.
12. Liu, Z.; Wang, F.; Chen, X. Integrin alpha(v)beta(3)-Targeted Cancer Therapy. *Drug Dev Res* 2008, 69, 329-339.
13. Niu, G.; Chen, X. Why integrin as a primary target for imaging and therapy. *Theranostics* 2011, 1, 30-47.
14. Chen, K.; Chen, X. Integrin targeted delivery of chemotherapeutics. *Theranostics* 2011, 1, 189-200.
15. Chen, X. Integrin Targeted Imaging and Therapy. *Theranostics* 2011, 2011, 28-29.
16. Chin, F. T.; Shen, B.; Liu, S.; Berganos, R. A.; Chang, E.; Mittra, E.; Chen, X.; Gambhir, S. S. First Experience with Clinical-Grade [(18) F]FPP(RGD) (2): An Automated Multi-step Radiosynthesis for Clinical PET Studies. *Mol Imaging Biol* 2011.
17. Gardlik, R.; Celec, P.; Bernadic, M. Targeting angiogenesis for cancer (gene) therapy. *Bratisl Lek Listy* 2011, 112, 428-34.
18. Meyer, A.; Auernheimer, J.; Modlinger, A.; Kessler, H. Targeting RGD recognizing integrins: drug development, biomaterial research, tumor imaging and targeting. *Curr Pharm Des* 2006, 12, 2723-47.
19. Belvisi, L.; Bernardi, A.; Colombo, M.; Manzoni, L.; Potenza, D.; Scolastico, C.; Giannini, G.; Marcellini, M.; Riccioni, T.; Castorina, M.; LoGiudice, P.; Pisano, C. Targeting integrins: insights into structure and activity of cyclic RGD pentapeptide mimics containing azabicycloalkane amino acids. *Bioorg Med Chem* 2006, 14, 169-80.
20. Schraa, A. J.; Kok, R. J.; Moorlag, H. E.; Bos, E. J.; Proost, J. H.; Meijer, D. K.; de Leij, L. F.; Molema, G. Targeting of RGD-modified proteins to tumor vasculature: a pharmacokinetic and cellular distribution study. *Int J Cancer* 2002, 102, 469-75.
21. Lee, S.; Xie, J.; Chen, X. Peptide-based probes for targeted molecular imaging. *Biochemistry* 2010, 49, 1364-76.
22. Lee, S.; Xie, J.; Chen, X. Peptides and peptide hormones for molecular imaging and disease diagnosis. *Chem Rev* 2010, 110, 3087-111.
23. Cai, W.; Chen, X. Anti-angiogenic cancer therapy based on integrin alphavbeta3 antagonism. *Anticancer Agents Med Chem* 2006, 6, 407-28.
24. Niu, Y.; Padhee, S.; Wu, H.; Bai, G.; Harrington, L.; Burda, W. N.; Shaw, L. N.; Cao, C.; Cai, J. Identification of gamma-AApeptides with potent and broad-spectrum antimicrobial activity. *Chem Commun (Camb)* 2011, 47, 12197-12199.
25. Niu, Y.; Jones, A.; Wu, H.; Varani, G.; Cai, J. Gamma-AApeptides bind to RNA by mimicking RNA-binding proteins. *Org Biomol Chem* 2011, 9, 6604-6609.
26. Niu, Y.; Hu, Y.; Li, X.; Chen, J.; Cai, J. Gamma AApeptides: Design, synthesis and evaluation. *New Journal of Chemistry* 2011, 35, 542-545.
27. Wu, Y. D.; Gellman, S. Peptidomimetics. *Accounts of Chemical Research* 2008, 41, 1231-1232.
28. Bergers, G.; Benjamin, L. E. Tumorigenesis and the angiogenic switch. *Nat Rev Cancer* 2003, 3, 401-10.
29. Pircher, A.; Hilbe, W.; Heidegger, I.; Drevs, J.; Tichelli, A.; Medinger, M. Biomarkers in tumor angiogenesis and anti-angiogenic therapy. *Int J Mol Sci* 2011, 12, 7077-99.
30. Ribatti, D.; Djonov, V. Angiogenesis in development and cancer today. *Int J Dev Biol* 2011, 55, 343-4.
31. Ribatti, D. Novel angiogenesis inhibitors: addressing the issue of redundancy in the angiogenic signaling pathway. *Cancer Treat Rev* 2011, 37, 344-52.
32. Gaitskell, K.; Martinek, I.; Bryant, A.; Kehoe, S.; Nicum, S.; Morrison, J. Angiogenesis inhibitors for the treatment of ovarian cancer. *Cochrane Database Syst Rev* 2011, 9, CD007930.
33. Prager, G. W.; Poettler, M. Angiogenesis in cancer. Basic mechanisms and therapeutic advances. *Hamostaseologie* 2011, 32.
34. Taeger, J.; Moser, C.; Hellerbrand, C.; Mycielska, M. E.; Glockzin, G.; Schlitt, H. J.; Geissler, E. K.; Stoeltzing, O.; Lang, S. A. Targeting FGFR/PDGFR/VEGFR Impairs Tumor Growth, Angiogenesis, and Metastasis by Effects on Tumor Cells, Endothelial Cells, and Pericytes in Pancreatic Cancer. *Mol Cancer Ther* 2011, 10, 2157-67.
35. Longatto Filho, A.; Lopes, J. M.; Schmitt, F. C. Angiogenesis and breast cancer. *J Oncol* 2010, 2010.
36. Belotti, D.; Foglieni, C.; Resovi, A.; Giavazzi, R.; Taraboletti, G. Targeting angiogenesis with compounds from the extracellular matrix. *Int J Biochem Cell Biol* 2011, 43, 1674-85.
37. Campbell, N. E.; Kellenberger, L.; Greenaway, J.; Moorehead, R. A.; Linnerth-Petrik, N. M.; Petrik, J. Extracellular matrix proteins and tumor angiogenesis. *J Oncol* 2010, 2010, 586905.
38. Eming, S. A.; Hubbell, J. A. Extracellular matrix in angiogenesis: dynamic structures with translational potential. *Exp Dermatol* 2011, 20, 605-13.
39. Gamble, L. J.; Borovjagin, A. V.; Matthews, Q. L. Role of RGD-containing ligands in targeting cellular integrins: Applications for ovarian cancer virotherapy (Review). *Exp Ther Med* 2010, 1, 233-240.
40. Kim, C.; Ye, F.; Ginsberg, M. H. Regulation of integrin activation. *Annu Rev Cell Dev Biol* 2011, 27, 321-45.
41. Margadant, C.; Monsuur, H. N.; Norman, J. C.; Sonnenberg, A. Mechanisms of integrin activation and trafficking. *Curr Opin Cell Biol* 2011, 23, 607-14.

42. Trabocchi, A.; Menchi, G.; Cini, N.; Bianchini, F.; Raspanti, S.; Bottoncetti, A.; Pupi, A.; Calorini, L.; Guarna, A. Click-chemistry-derived triazole ligands of arginine-glycine-aspartate (RGD) integrins with a broad capacity to inhibit adhesion of melanoma cells and both in vitro and in vivo angiogenesis. *J Med Chem* 2010, 53, 7119-28.

43. Reardon, D. A.; Neyns, B.; Weller, M.; Tonn, J. C.; Nabors, L. B.; Stupp, R. Cilengitide: an RGD pentapeptide alphanubeta3 and alphanubeta5 integrin inhibitor in development for glioblastoma and other malignancies. *Future Oncol* 2011, 7, 339-54.

44. Sulyok, G. b. A. G.; Gibson, C.; Goodman, S. L.; Holzemann, G. n.; Wiesner, M.; Kessler, H. Solid-Phase Synthesis of a Nonpeptide RGD Mimetic Library: New Selective alphavbeta3 Integrin Antagonists. *Journal of Medicinal Chemistry* 2001, 44, 1938-1950.

45. Chen, X.; Liu, S.; Hou, Y.; Tohme, M.; Park, R.; Bading, J. R.; Conti, P. S. MicroPET imaging of breast cancer alphav-integrin expression with 64Cu-labeled dimeric RGD peptides. *Mol Imaging Biol* 2004, 6, 350-9.

46. Chen, X.; Tohme, M.; Park, R.; Hou, Y.; Bading, J. R.; Conti, P. S. Micro-PET imaging of alphavbeta3-integrin expression with 18F-labeled dimeric RGD peptide. *Mol Imaging* 2004, 3, 96-104.

47. Chen, X.; Plasencia, C.; Hou, Y.; Neamati, N. Synthesis and biological evaluation of dimeric RGD peptide-paclitaxel conjugate as a model for integrin-targeted drug delivery. *J Med Chem* 2005, 48, 1098-106.

48. Cai, W.; Zhang, X.; Wu, Y.; Chen, X. A thiol-reactive 18F-labeling agent, N-[2-(4-18F-fluorobenzamido)ethyl]maleimide, and synthesis of RGD peptide-based tracer for PET imaging of alpha v beta 3 integrin expression. *J Nucl Med* 2006, 47, 1172-80.

49. Wu, Y.; Cai, W.; Chen, X. Near-infrared fluorescence imaging of tumor integrin alpha v beta 3 expression with Cy7-labeled RGD multimers. *Mol Imaging Biol* 2006, 8, 226-36.

50. Li, Z. B.; Cai, W.; Cao, Q.; Chen, K.; Wu, Z.; He, L.; Chen, X. (64)Cu-labeled tetrameric and octameric RGD peptides for small-animal PET of tumor alpha(v)beta(3) integrin expression. *J Nucl Med* 2007, 48, 1162-71.

51. Li, Z. B.; Wu, Z.; Chen, K.; Chin, F. T.; Chen, X. Click chemistry for (18)F-labeling of RGD peptides and microPET imaging of tumor integrin alphavbeta3 expression. *Bioconjug Chem* 2007, 18, 1987-94.

52. Li, Z. B.; Chen, K.; Chen, X. (68)Ga-labeled multimeric RGD peptides for microPET imaging of integrin alpha(v)beta(3) expression. *Eur J Nucl Med Mol Imaging* 2008, 35, 1100-8.

53. Wang, H.; Chen, K.; Cai, W.; Li, Z.; He, L.; Kashefi, A.; Chen, X. Integrin-targeted imaging and therapy with RGD4C-TNF fusion protein. *Mol Cancer Ther* 2008, 7, 1044-53.

54. Xie, J.; Chen, K.; Lee, H. Y.; Xu, C.; Hsu, A. R.; Peng, S.; Chen, X.; Sun, S. Ultrasmall c(RGDyK)-coated Fe3O4 nanoparticles and their specific targeting to integrin alpha(v)beta3-rich tumor cells. *J Am Chem Soc* 2008, 130, 7542-3.

55. Liu, Z.; Liu, S.; Niu, G.; Wang, F.; Liu, S.; Chen, X. Optical imaging of integrin alphavbeta3 expression with near-infrared fluorescent RGD dimer with tetra(ethylene glycol) linkers. *Mol Imaging* 2010, 9, 21-9.

56. Jacobson, O.; Zhu, L.; Niu, G.; Weiss, I. D.; Szajek, L. P.; Ma, Y.; Sun, X.; Yan, Y.; Kiesewetter, D. O.; Liu, S.; Chen, X. MicroPET Imaging of Integrin alpha(v)beta (3) Expressing Tumors Using (89)Zr-RGD Peptides. *Mol Imaging Biol* 2011, 13, 1224-33.

57. Deng, C.; Tian, H.; Zhang, P.; Sun, J.; Chen, X.; Jing, X. Synthesis and characterization of RGD peptide grafted poly(ethylene glycol)-b-poly(L-lactide)-b-poly(L-glutamic acid) triblock copolymer. *Biomacromolecules* 2006, 7, 590-6.

58. Chen, X.; Park, R.; Hou, Y.; Khankaldyyan, V.; Gonzales-Gomez, I.; Tohme, M.; Bading, J. R.; Laug, W. E.; Conti, P. S. MicroPET imaging of brain tumor angiogenesis with 18F-labeled PEGylated RGD peptide. *Eur J Nucl Med Mol Imaging* 2004, 31, 1081-9.

59. Yan, Y.; Chen, K.; Yang, M.; Sun, X.; Liu, S.; Chen, X. A new 18F-labeled BBN-RGD peptide heterodimer with a symmetric linker for prostate cancer imaging. *Amino Acids* 2011, 41, 439-47.

60. Liu, Z.; Niu, G.; Wang, F.; Chen, X. (68)Ga-labeled NOTA-RGD-BBN peptide for dual integrin and GRPR-targeted tumor imaging. *Eur J Nucl Med Mol Imaging* 2009, 36, 1483-94.

61. Mittra, E. S.; Goris, M. L.; Iagaru, A. H.; Kardan, A.; Burton, L.; Berganos, R.; Chang, E.; Liu, S.; Shen, B.; Chin, F. T.; Chen, X.; Gambhir, S. S. Pilot pharmacokinetic and dosimetric studies of (18)F-FPPRGD2: a PET radiopharmaceutical agent for imaging alpha(v)beta(3) integrin levels. *Radiology* 2011, 260, 182-91.

62. Chen, X.; Park, R.; Shahinian, A. H.; Bading, J. R.; Conti, P. S. Pharmacokinetics and tumor retention of 125I-labeled RGD peptide are improved by PEGylation. *Nucl Med Biol* 2004, 31, 11-9.

63. Chen, X.; Park, R.; Shahinian, A. H.; Tohme, M.; Khankaldyyan, V.; Bozorgzadeh, M. H.; Bading, J. R.; Moats, R.; Laug, W. E.; Conti, P. S. 18F-labeled RGD peptide: initial evaluation for imaging brain tumor angiogenesis. *Nucl Med Biol* 2004, 31, 179-89.

64. Li, Z. B.; Wu, Z.; Chen, K.; Ryu, E. K.; Chen, X. 18F-labeled BBN-RGD heterodimer for prostate cancer imaging. *J Nucl Med* 2008, 49, 453-61.

65. Jiang, T.; Zhang, C.; Zheng, X.; Xu, X.; Xie, X.; Liu, H.; Liu, S. Noninvasively characterizing the different alphavbeta3 expression patterns in lung cancers with RGD-USPIO using a clinical 3.0T MR scanner. *Int J Nanomedicine* 2009, 4, 241-9.

66. Chen, X.; Sievers, E.; Hou, Y.; Park, R.; Tohme, M.; Bart, R.; Bremner, R.; Bading, J. R.; Conti, P. S. Integrin alpha v beta 3-targeted imaging of lung cancer. *Neoplasia* 2005, 7, 271-9.

67. Haubner, R.; Kuhnast, B.; Mang, C.; Weber, W. A.; Kessler, H.; Wester, H. J.; Schwaiger, M. [18F]Galacto-RGD: synthesis, radiolabeling, metabolic stability, and radiation dose estimates. *Bioconjug Chem* 2004, 15, 61-9.

68. Hultsch, C.; Schottelius, M.; Auernheimer, J.; Alke, A.; Wester, H. J. (18)F-Fluoroglucosylation of peptides, exemplified on cyclo(RGDfK). *Eur J Nucl Med Mol Imaging* 2009, 36, 1469-74.

69. Liu, Z.; Liu, S.; Wang, F.; Liu, S.; Chen, X. Noninvasive imaging of tumor integrin expression using (18)F-labeled RGD dimer peptide with PEG (4) linkers. *Eur J Nucl Med Mol Imaging* 2009, 36, 1296-307.

70. Wu, Z.; Li, Z. B.; Chen, K.; Cai, W.; He, L.; Chin, F. T.; Li, F.; Chen, X. microPET of tumor integrin alphavbeta3 expression using 18F-labeled PEGylated tetrameric RGD peptide (18F-FPRGD4). *J Nucl Med* 2007, 48, 1536-44.

71. Liu, Z.; Shi, J.; Jia, B.; Yu, Z.; Liu, Y.; Zhao, H.; Li, F.; Tian, J.; Chen, X.; Liu, S.; Wang, F. Two Y-labeled multimeric RGD peptides RGD4 and 3PRGD2 for integrin targeted radionuclide therapy. *Mol Pharm* 2011, 8, 591-9.

72. Thumshirn, G.; Hersel, U.; Goodman, S. L.; Kessler, H. Multimeric cyclic RGD peptides as potential tools for tumor targeting: solid-phase peptide synthesis and chemoselective oxime ligation. *Chemistry* 2003, 9, 2717-25.
73. Liu, S. Radiolabeled multimeric cyclic RGD peptides as integrin alphavbeta3 targeted radiotracers for tumor imaging. *Mol Pharm* 2006, 3, 472-87.
74. Sancey, L.; Garanger, E.; Foillard, S.; Schoehn, G.; Hurbin, A.; Albiges-Rizo, C.; Boturyn, D.; Souchier, C.; Grichine, A.; Dumy, P.; Coll, J. L. Clustering and internalization of integrin alphavbeta3 with a tetrameric RGD-synthetic peptide. *Mol Ther* 2009, 17, 837-43.
75. Auzzas, L.; Zanardi, F.; Battistini, L.; Burreddu, P.; Carta, P.; Rassu, G.; Curti, C.; Casiraghi, G. Targeting alphav-beta3 integrin: design and applications of mono- and multifunctional RGD-based peptides and semipeptides. *Curr Med Chem* 2010, 17, 1255-99.
76. Niu, Y.; Hu, Y.; Li, X.; Chen, J.; Cai, J. g-AApeptides: design, synthesis and evaluation. *New J Chem* 2011, 35, 542-5.
77. Niu, Y.; Jones, A. J.; Wu, H.; Varani, G.; Cai, J. gamma-AApeptides bind to RNA by mimicking RNA-binding proteins. *Org Biomol Chem* 2011, 9, 6604-9.
78. Niu, Y.; Padhee, S.; Wu, H.; Bai, G.; Harrington, L.; Burda, W. N.; Shaw, L. N.; Cao, C.; Cai, J. Identification of gamma-AApeptides with potent and broad-spectrum antimicrobial activity. *Chem Commun (Camb)* 2011, 47, 12197-9.
79. Ruegg, C.; Hasmim, M.; Lejeune, F. J.; Alghisi, G. C. Antiangiogenic peptides and proteins: from experimental tools to clinical drugs. *Biochim Biophys Acta* 2006, 1765, 155-77.
80. Germer, M.; Kanse, S. M.; Kirkegaard, T.; Kjoller, L.; Felding-Habermann, B.; Goodman, S.; Preissner, K. T. Kinetic analysis of integrin-dependent cell adhesion on vitronectin—the inhibitory potential of plasminogen activator inhibitor-1 and RGD peptides. *Eur J Biochem* 1998, 253, 669-74.
81. Hariharan, S.; Gustafson, D.; Holden, S.; McConkey, D.; Davis, D.; Morrow, M.; Basche, M.; Gore, L.; Zang, C.; O'Bryant, C. L.; Baron, A.; Gallemann, D.; Colevas, D.; Eckhardt, S. G. Assessment of the biological and pharmacological effects of the alpha nu beta3 and alpha nu beta5 integrin receptor antagonist, cilengitide (EMD 121974), in patients with advanced solid tumors. *Ann Oncol* 2007, 18, 1400-7.
82. Taga, T.; Suzuki, A.; Gonzalez-Gomez, I.; Gilles, F. H.; Stins, M.; Shimada, H.; Barsky, L.; Weinberg, K. I.; Laug, W. E. αv-Integrin antagonist EMD 121974 induces apoptosis in brain tumor cells growing on vitronectin and tenascin. *International Journal of Cancer* 2002, 98, 690-697.
83. Kimura, R. H.; Levin, A. M.; Cochran, F. V.; Cochran, J. R. Engineered cystine knot peptides that bind αvβ3, αvβ5, and α5β1 integrins with low-nanomolar affinity. *Proteins: Structure, Function, and Bioinformatics* 2009, 77, 359-369.
84. Ye, Y.; Chen, X. Integrin targeting for tumor optical imaging. *Theranostics* 2011, 1, 102-26.
85. Dresner-Pollak, R.; Rosenblatt, M. Blockade of osteoclast-mediated bone resorption through occupancy of the integrin receptor: A potential approach to the therapy of osteoporosis. *Journal of Cellular Biochemistry* 1994, 56, 323-330.
86. Stockbauer, K. E.; Magoun, L.; Liu, M.; Burns, E. H.; Gubba, S.; Renish, S.; Pan, X.; Bodary, S. C.; Baker, E.; Coburn, J.; Leong, J. M.; Musser, J. M. A natural variant of the cysteine protease virulence factor of group A *Streptococcus* with an arginine-glycine-aspartic acid (RGD) motif preferentially binds human integrins alphavbeta3 and alphaIIbbeta3. *Proceedings of the National Academy of Sciences* 1999, 96, 242-247.
87. Cai, W.; Shin, D. W.; Chen, K.; Gheysens, O.; Cao, Q.; Wang, S. X.; Gambhir, S. S.; Chen, X. Peptide-labeled near-infrared quantum dots for imaging tumor vasculature in living subjects. *Nano Lett* 2006, 6, 669-676.
88. Cai, W.; Wu, Y.; Chen, K.; Cao, Q.; Tice, D. A.; Chen, X. In vitro and in vivo characterization of $^{64}$Cu-labeled Abegrin™, a humanized monoclonal antibody against integrin $a_vb_3$. *Cancer Res* 2006, 66, 9673-81.
89. Yang, X.; Hong, H.; Grailer, J. J.; Rowland, I. J.; Javadi, A.; Hurley, S. A.; Xiao, Y.; Yang, Y.; Zhang, Y.; Nickles, R. J.; Cai, W.; Steeber, D. A.; Gong, S. cRGD-functionalized, DOX-conjugated, and $^{64}$Cu-labeled superparamagnetic iron oxide nanoparticles for targeted anticancer drug delivery and PET/MR imaging. *Biomaterials* 2011, 32, 4151-60.
90. Hong, H.; Severin, G. W.; Yang, Y.; Engle, J. W.; Zhang, Y.; Barnhart, T. E.; Liu, G.; Leigh, B. R.; Nickles, R. J.; Cai, W. Positron emission tomography imaging of CD105 expression with $^{89}$Zr-Df-TRC105. *Eur J Nucl Med Mol Imaging* 2011, DOI: 10.1007/s00259-011-1930-x, ASAP.
91. Hu, Y.; Li, X.; Sebti, S. M.; Chen, J.; Cai, J. Design and synthesis of AApeptides: a new class of peptide mimics. *Bioorg Med Chem Lett* 2011, 21, 1469-71.
92. Zhou, Y.; Chakraborty, S.; Liu, S. Radiolabeled Cyclic RGD Peptides as Radiotracers for Imaging Tumors and Thrombosis by SPECT. *Theranostics* 2011, 1, 58-82.
93. Lin, H. Y.; Lansing, L.; Merillon, J. M.; Davis, F. B.; Tang, H. Y.; Shih, A.; Vitrac, X.; Krisa, S.; Keating, T.; Cao, H. J.; Bergh, J.; Quackenbush, S.; Davis, P. J. Integrin alphaV-beta3 contains a receptor site for resveratrol. *Faseb J* 2006, 20, 1742-4.
94. Arnold, M.; Hirschfeld-Warneken, V. C.; Lohmuller, T.; Heil, P.; Blummel, J.; Cavalcanti-Adam, E. A.; Lopez-Garcia, M.; Walther, P.; Kessler, H.; Geiger, B.; Spatz, J. P. Induction of cell polarization and migration by a gradient of nanoscale variations in adhesive ligand spacing. *Nano Lett* 2008, 8, 2063-9.
95. Balasubramanian, S.; Kuppuswamy, D. RGD-containing peptides activate S6K1 through beta3 integrin in adult cardiac muscle cells. *J Biol Chem* 2003, 278, 42214-24.
96. Iera, J. A.; Jenkins, L. M. M.; Kajiyama, H.; Kopp, J. B.; Appella, D. H. Solid-phase synthesis and screening of N-acylated polyamine (NAPA) combinatorial libraries for protein binding. *Bioorganic & Medicinal Chemistry Letters* 2010, 20, 6500-6503.
97. Hayashi, R.; Wang, D.; Hara, T.; Iera, J. A.; Durell, S. R.; Appella, D. H. N-Acylpolyamine inhibitors of HDM2 and HDMX binding to p53. *Bioorganic & Medicinal Chemistry* 2009, 17, 7884-7893.
98. Mas-Moruno, C.; Beck, J. G.; Doedens, L.; Frank, A. O.; Marinelli, L.; Cosconati, S.; Novellino, E.; Kessler, H. Increasing alphavbeta3 selectivity of the anti-angiogenic drug cilengitide by N-methylation. *Angew Chem Int Ed Engl* 2011, 50, 9496-500.
99. Cai, J.; Rosenzweig, B. A.; Hamilton, A. D. Inhibition of chymotrypsin by a self-assembled DNA quadruplex functionalized with cyclic peptide binding fragments. *Chemistry* 2009, 15, 328-32.
100. Cai, W.; Sam Gambhir, S.; Chen, X. Multimodality tumor imaging targeting integrin alphavbeta3. *Biotechniques* 2005, 39, S14-25.

101. Zhang, X.; Xiong, Z.; Wu, Y.; Cai, W.; Tseng, J. R.; Gambhir, S. S.; Chen, X. Quantitative PET imaging of tumor integrin alphavbeta3 expression with 18F-FRGD2. *J Nucl Med* 2006, 47, 113-21.
102. Hsu, A. R.; Veeravagu, A.; Cai, W.; Hou, L. C.; Tse, V.; Chen, X. Integrin alpha v beta 3 antagonists for anti-angiogenic cancer treatment. *Recent Pat Anticancer Drug Discov* 2007, 2, 143-58.
103. Wu, Z.; Li, Z. B.; Cai, W.; He, L.; Chin, F. T.; Li, F.; Chen, X. 18F-labeled mini-PEG spacered RGD dimer (18F-FPRGD2): synthesis and microPET imaging of alphavbeta3 integrin expression. *Eur J Nucl Med Mol Imaging* 2007, 34, 1823-31.
104. Veeravagu, A.; Liu, Z.; Niu, G.; Chen, K.; Jia, B.; Cai, W.; Jin, C.; Hsu, A. R.; Connolly, A. J.; Tse, V.; Wang, F.; Chen, X. Integrin alphavbeta3-targeted radioimmunotherapy of glioblastoma multiforme. *Clin Cancer Res* 2008, 14, 7330-9.
105. Cai, W.; Chen, X. Anti-angiogenic cancer therapy based on integrin a$_v$b$_3$ antagonism. *Anti-Cancer Agents Med Chem* 2006, 6, 407-428.
106. Niu, G.; Xiong, Z.; Cheng, Z.; Cai, W.; Gambhir, S. S.; Xing, L.; Chen, X. In vivo bioluminescence tumor imaging of RGD peptide-modified adenoviral vector encoding firefly luciferase reporter gene. *Mol Imaging Biol* 2007, 9, 126-34.
107. Cai, W.; Niu, G.; Chen, X. Imaging of integrins as biomarkers for tumor angiogenesis. *Curr Pharm Des* 2008, 14, 2943-73.
108. Cai, W.; Chen, X. Multimodality molecular imaging of tumor angiogenesis. *J Nucl Med* 2008, 49 Suppl 2, 113S-28S.
109. Hong, H.; Shi, J.; Yang, Y.; Zhang, Y.; Engle, J. W.; Nickles, R. J.; Wang, X.; Cai, W. Cancer-Targeted Optical Imaging with Fluorescent Zinc Oxide Nanowires. *Nano Letters* 2011, 11, 3744-3750.
110. Marugan, J. J.; Manthey, C.; Anaclerio, B.; Lafrance, L.; Lu, T.; Markotan, T.; Leonard, K. A.; Crysler, C.; Eisennagel, S.; Dasgupta, M.; Tomczuk, B. Design, synthesis, and biological evaluation of novel potent and selective alphavbeta3/alphavbeta5 integrin dual inhibitors with improved bioavailability. Selection of the molecular core. *J Med Chem* 2005, 48, 926-34.
111. Stragies, R.; Osterkamp, F.; Zischinsky, G.; Vossmeyer, D.; Kalkhof, H.; Reimer, U.; Zahn, G. Design and synthesis of a new class of selective integrin alpha5beta1 antagonists. *J Med Chem* 2007, 50, 3786-94.
112. Heikkila, O.; Susi, P.; Stanway, G.; Hyypia, T. Integrin alphaVbeta6 is a high-affinity receptor for coxsackievirus A9. *J Gen Virol* 2009, 90, 197-204.
113. Cai, W.; Chen, K.; Mohamedali, K. A.; Cao, Q.; Gambhir, S. S.; Rosenblum, M. G.; Chen, X. PET of vascular endothelial growth factor receptor expression. *J Nucl Med* 2006, 47, 2048-56.
114. Cai, W.; Chen, K.; He, L.; Cao, Q.; Koong, A.; Chen, X. Quantitative PET of EGFR expression in xenograft-bearing mice using 64Cu-labeled cetuximab, a chimeric anti-EGFR monoclonal antibody. *Eur J Nucl Med Mol Imaging* 2007, 34, 850-8.

In regard to the discussion herein including the Examples above and the claims, it should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to measurement techniques and the units of the numerical value. In addition, the phrase "about 'x' to 'y'" includes "about 'x' to about 'y'".

Many variations and modifications may be made to the above-described embodiments. All such modifications and variations are intended to be included herein within the scope of this disclosure and protected by the following claims.

We claim:
1. A peptidomimetic compound comprising:
   a γ-AApeptide capable of binding an RGD binding site on integrin α$_v$β$_3$, the γ-AApeptide compound comprising a γ-AApeptide having the structure of Formula I:

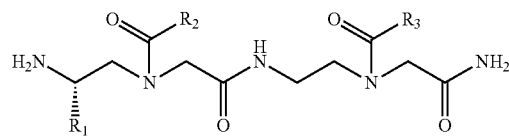

Formula I wherein R1 is a moiety selected from the group of moieties consisting of:
   hydrogen, methyl,

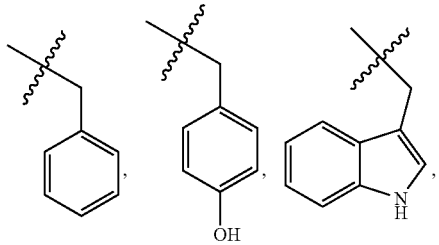

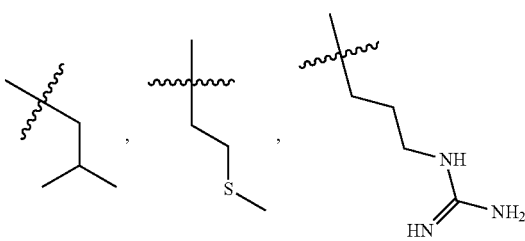

-continued

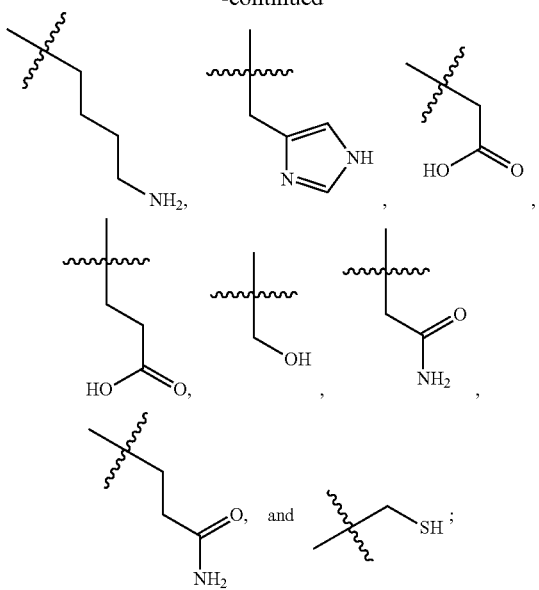

wherein R2 is a moiety selected from the group of moieties consisting of:

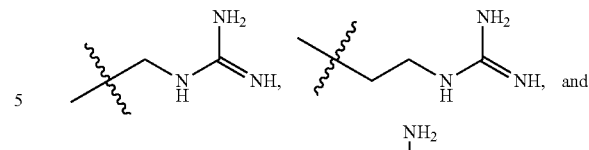

and
wherein R3 is a moiety selected from the group of moieties consisting of:

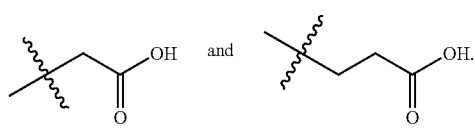 [SMILES: *CC(=O)O ; *CCC(=O)O]

2. The γ-AApeptide compound of claim 1, wherein the γ-AApeptide compound is selected from the group of compounds consisting of compounds: γ-AA1, γ-AA2, γ-AA3, γ-AA4, γ-AA5, and γ-AA7 having the structures shown below:

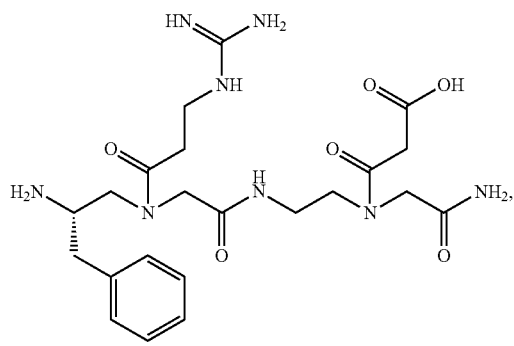

γ-AA2

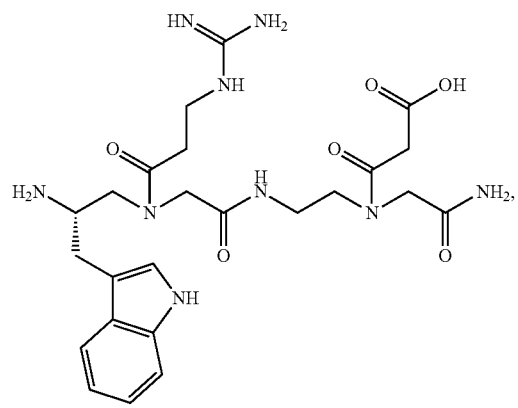

γ-AA4

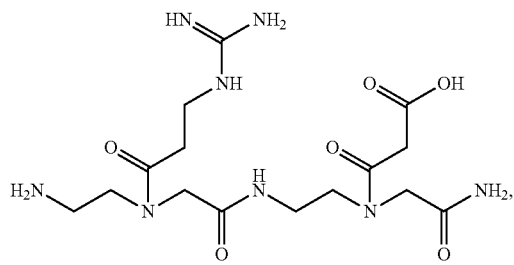

γ-AA1

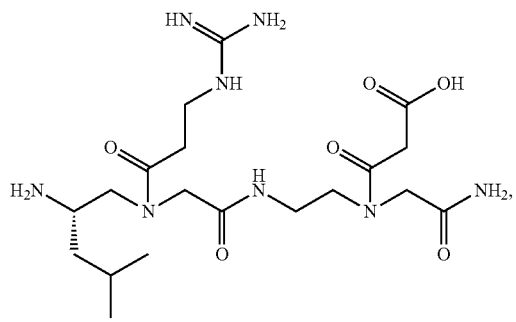

γ-AA3

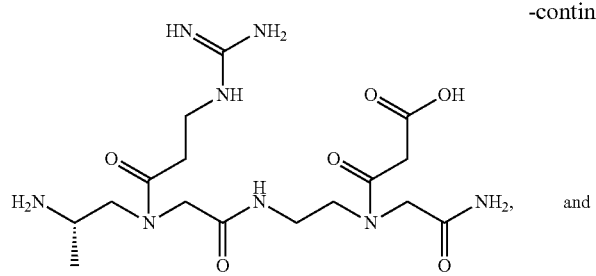
and
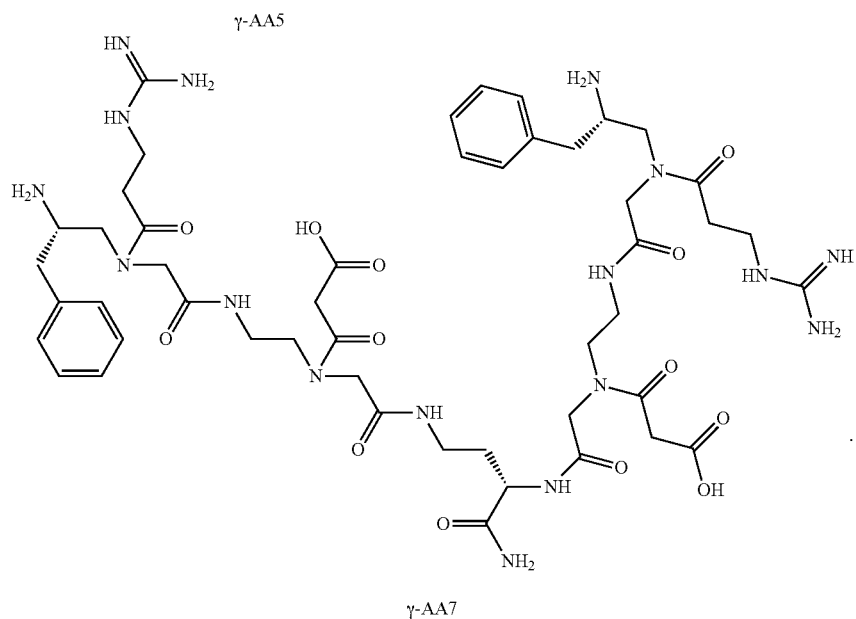
γ-AA5
γ-AA7
3. The γ-AApeptide compound of claim 1, the γ-AApeptide compound comprising: a multimeric γ-AApeptide compound comprising two or more γ-AApeptide units of Formula I joined by a linker, wherein Formula I has the structure:
Formula I
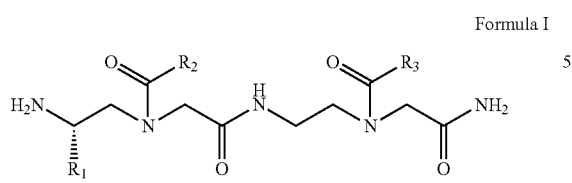
wherein R1 is a moiety selected from the group of moieties consisting of:
hydrogen, methyl,
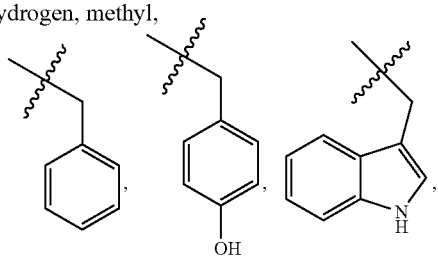
-continued
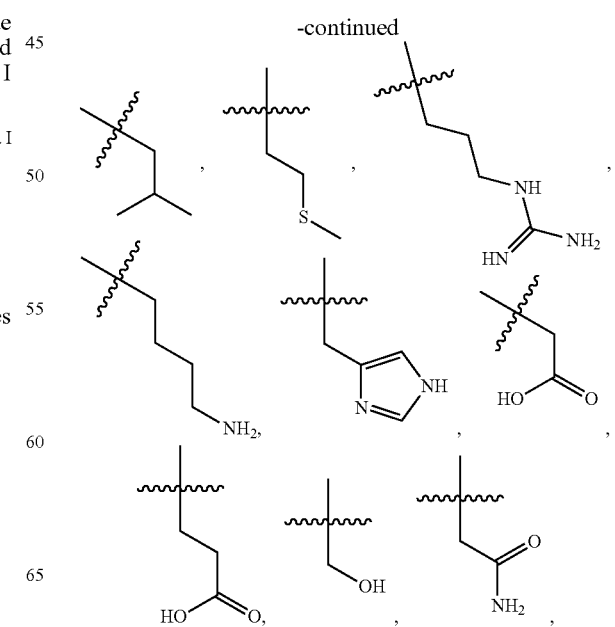

-continued

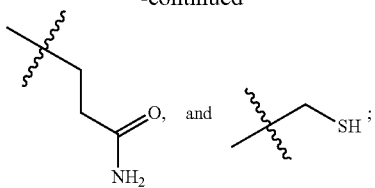

wherein R2 is a moiety selected from the group of moieties consisting of:

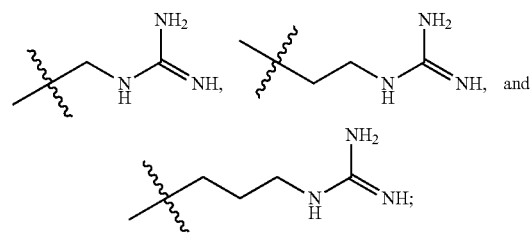

and
wherein R3 is a moiety selected from the group of moieties consisting of:

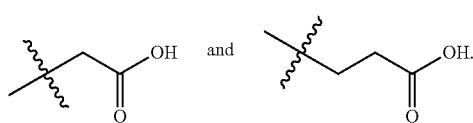

4. The multimeric γ-AApeptide compound of claim 3 selected from the dimeric γ-AApeptide having the structure of Formula II and the tetrameric γ-AApeptide having the structure of Formula III:

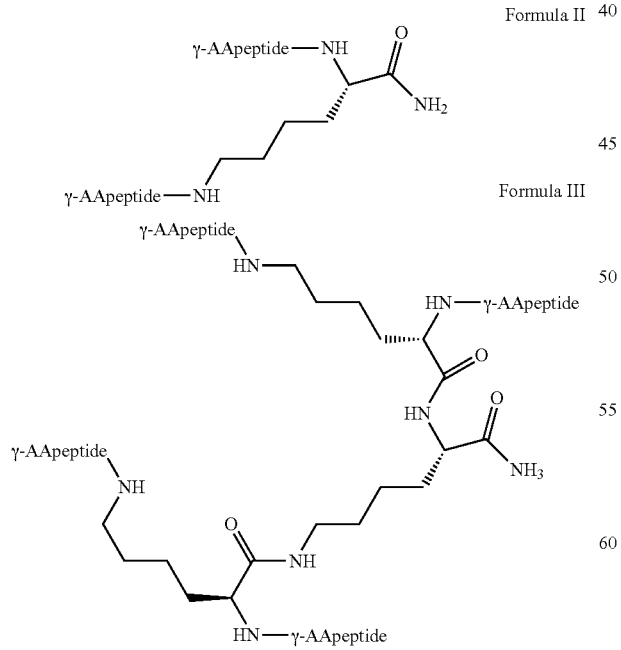

wherein each γ-AApeptide unit is independently selected from a γ-AApeptide of Formula I.

5. The γ-AApeptide compound of claim 1 further comprising:
a detectable label; and
a linker connecting the detectable label and the γ-AApeptide.

6. The γ-AApeptide compound of claim 5, wherein the detectable label is a radiolabel.

7. The γ-AApeptide compound of claim 6, wherein the radiolabel is $^{64}$Cu.

8. The γ-AApeptide compound of claim 5, wherein the linker is selected from the group of linkers consisting of: DOTA and NOTA.

9. The γ-AApeptide compound of claim 6, wherein the radiolabeled γ-AApeptide compound can be detected by a PET scanning device.

10. A kit comprising a γ-AApeptide compound coupled to a detectable label and instructions for use of the labeled γ-AApeptide compound, wherein the γ-AApeptide compound has the structure of Formula I:

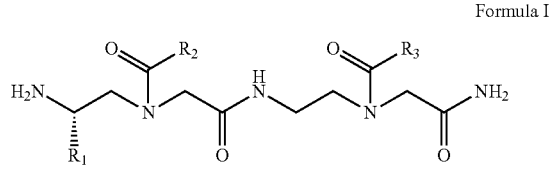

Formula I wherein R1 is a moiety selected from the group of moieties consisting of:
hydrogen, methyl,

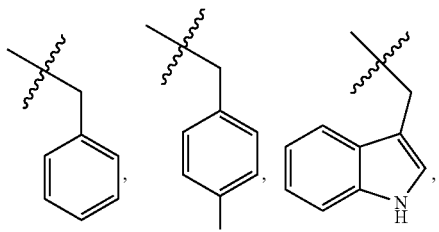

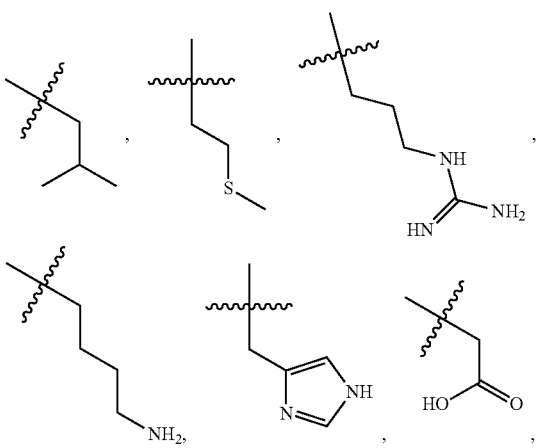

-continued

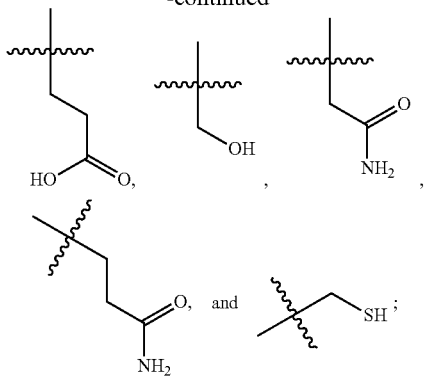

wherein R2 is a moiety selected from the group of moieties consisting of:

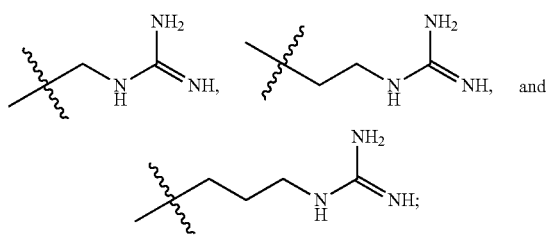

and wherein R3 is a moiety selected from the group of moieties consisting of:

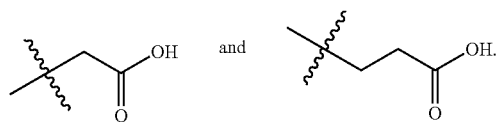 [SMILES: *CC(=O)O ; *CCC(=O)O]

11. A pharmaceutical composition comprising:

a γ-AApeptide compound capable of binding an RGD binding site on integrin $α_vβ_3$, or a pharmaceutically acceptable salt, solvate or hydrate of the γ-AApeptide compound, and a pharmaceutically acceptable carrier, wherein the γ-AApeptide compound has the structure of Formula I:

Formula I wherein R1 is a moiety selected from the group of moieties consisting of:

hydrogen, methyl,

wherein R2 is a moiety selected from the group of moieties consisting of:

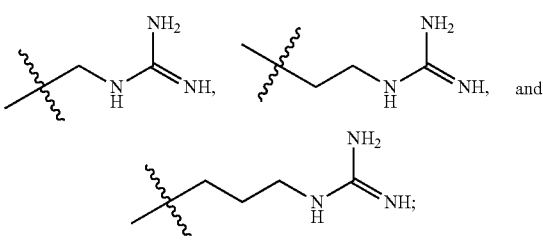

and wherein R3 is a moiety selected from the group of moieties consisting of:

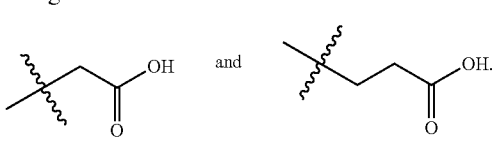

* * * * *